US009709260B2

(12) United States Patent
Ueno et al.

(10) Patent No.: US 9,709,260 B2
(45) Date of Patent: Jul. 18, 2017

(54) HEAT GENERATING DEVICE

(75) Inventors: Satoshi Ueno, Tochigi (JP); Hideo Kobayashi, Tochigi (JP); Kazutoshi Ootsuka, Tochigi (JP)

(73) Assignee: KAO CORPORATION, Tokyo (JP)

( * ) Notice: Subject to any disclaimer, the term of this patent is extended or adjusted under 35 U.S.C. 154(b) by 1191 days.

(21) Appl. No.: 13/704,914

(22) PCT Filed: Jun. 16, 2011

(86) PCT No.: PCT/JP2011/063853
§ 371 (c)(1),
(2), (4) Date: Jan. 29, 2013

(87) PCT Pub. No.: WO2011/158919
PCT Pub. Date: Dec. 22, 2011

(65) Prior Publication Data
US 2013/0125837 A1    May 23, 2013

(30) Foreign Application Priority Data

Jun. 18, 2010 (JP) ................................. 2010-140013
Jun. 18, 2010 (JP) ................................. 2010-140014
(Continued)

(51) Int. Cl.
*F22B 1/00* (2006.01)
*B65B 1/04* (2006.01)
(Continued)

(52) U.S. Cl.
CPC ................ *F22B 1/00* (2013.01); *A61F 7/034* (2013.01); *B65B 1/04* (2013.01); *B65B 3/00* (2013.01);
(Continued)

(58) Field of Classification Search
None
See application file for complete search history.

(56) References Cited

U.S. PATENT DOCUMENTS 3,476,937 A * 11/1969 Vrancken ................ B41C 1/055
101/470
4,205,957 A * 6/1980 Fujiwara .................... F24J 1/00
126/263.02
(Continued)

FOREIGN PATENT DOCUMENTS

CN        101161219 A     4/2008
JP        7-59809 A       3/1995
(Continued)

OTHER PUBLICATIONS

International Preliminary Report on Patentability for International Patent Application No. PCT/JP2011/063853, dated Jan. 24, 2013.
(Continued)

*Primary Examiner* — Gregory Huson
*Assistant Examiner* — Eric Gorman
(74) *Attorney, Agent, or Firm* — Birch, Stewart, Kolasch & Birch, LLP

(57) ABSTRACT

A heat generating device including a heat generating element and an enclosing material entirely enclosing the heat generating element. The heat generating element includes a base sheet formed of a fibrous sheet containing superabsorbent polymer particles and hydrophilic fibers and a layer of a heat generative composition containing oxidizable metal particles on a side of the base sheet. The enclosing material includes a first cover sheet and a second cover sheet bonded together in their peripheral portions to provide a space therebetween in which the heat generating member is placed. The heat generating element in the space is in a non-fixed state to the enclosing material. The first cover sheet has air permeability in part and is disposed on the side of the layer of the heat generative composition. The heat generating device is capable of releasing steam from the side of the first cover sheet during use.

15 Claims, 16 Drawing Sheets

(30) Foreign Application Priority Data

Jun. 18, 2010 (JP) ................................ 2010-140015
Jun. 25, 2010 (JP) ................................ 2010-145689

(51) Int. Cl.

| | | |
|---|---|---|
| B65B 3/00 | (2006.01) | |
| F24J 1/00 | (2006.01) | |
| A61F 7/00 | (2006.01) | |
| A61F 7/08 | (2006.01) | |
| C09K 5/18 | (2006.01) | |
| A61F 7/03 | (2006.01) | |
| A61F 7/02 | (2006.01) | |

(52) U.S. Cl.

CPC ......... *F24J 1/00* (2013.01); *A61F 2007/0098* (2013.01); *A61F 2007/026* (2013.01); *A61F 2007/0214* (2013.01); *A61F 2007/0258* (2013.01)

(56) References Cited

U.S. PATENT DOCUMENTS

| | | | | |
|---|---|---|---|---|
| 4,268,272 | A * | 5/1981 | Taura ................ | A47J 36/28 126/204 |
| 4,399,009 | A * | 8/1983 | Chisholm ............. | C08J 5/2281 204/266 |
| RE32,026 | E * | 11/1985 | Yamashita ............. | A61F 7/034 126/204 |
| 5,225,236 | A * | 7/1993 | Keusch ................. | B32B 27/12 128/849 |
| 5,277,180 | A * | 1/1994 | Angelillo .............. | A61F 7/03 604/358 |
| 5,807,370 | A * | 9/1998 | Igaue ............... | A61F 13/51305 442/402 |
| 5,879,378 | A * | 3/1999 | Usui ................. | A61F 7/034 126/263.02 |
| 6,127,294 | A | 10/2000 | Koiso et al. | |
| 6,436,128 | B1 | 8/2002 | Usui | |
| 6,761,994 | B2 * | 7/2004 | Yamashita .............. | B32B 7/12 156/334 |
| 7,611,767 | B2 * | 11/2009 | Usui ................. | A61F 7/034 126/263.01 |
| 7,652,228 | B2 * | 1/2010 | Igaki ................. | A61F 7/034 126/204 |
| 7,686,840 | B2 * | 3/2010 | Quincy, III .............. | A61F 7/03 428/340 |
| 7,763,061 | B2 * | 7/2010 | Schorr ................. | A61F 7/034 607/108 |
| 8,197,526 | B2 * | 6/2012 | Kumamoto ............. | A61F 7/034 607/111 |
| 8,343,203 | B2 * | 1/2013 | Ishikawa ................ | A61F 7/034 424/443 |
| 8,425,578 | B2 * | 4/2013 | Quincy, III ............ | A61F 7/034 126/262 |
| 8,430,921 | B2 * | 4/2013 | Wong ................. | A61F 7/034 607/108 |
| 8,916,266 | B2 * | 12/2014 | Takanohashi ........ | C08F 230/08 428/144 |
| 2002/0121624 | A1 | 9/2002 | Usui | |
| 2004/0042965 | A1 * | 3/2004 | Usui .................. | A61F 7/034 424/40 |
| 2005/0000827 | A1 | 1/2005 | Matsui et al. | |
| 2005/0019668 | A1 * | 1/2005 | Yamamoto ............ | C08J 5/2231 429/317 |
| 2005/0277007 | A1 * | 12/2005 | Yoshitake ........... | H01M 8/1004 429/450 |
| 2007/0020412 | A1 | 1/2007 | Kumamoto et al. | |
| 2007/0156213 | A1 | 7/2007 | Friedensohn et al. | |
| 2007/0267583 | A1 * | 11/2007 | Dodo ................ | A61F 7/034 250/493.1 |
| 2007/0267595 | A1 * | 11/2007 | Dodo ................ | A61F 7/034 252/67 |
| 2007/0277806 | A1 * | 12/2007 | Dodo .................. | A61F 7/034 126/263.02 |
| 2008/0003519 | A1 * | 1/2008 | Felder ................. | B41M 5/41 430/200 |
| 2008/0029079 | A1 * | 2/2008 | Dodo .................. | A61F 7/034 126/263.01 |
| 2008/0029080 | A1 * | 2/2008 | Dodo .................. | A61F 7/034 126/263.02 |
| 2008/0087271 | A1 | 4/2008 | Ajiri et al. | |
| 2008/0200971 | A1 * | 8/2008 | Dodo .................. | A61F 7/034 607/108 |
| 2008/0202490 | A1 * | 8/2008 | Dodo .................. | A61F 7/034 126/263.07 |
| 2008/0206549 | A1 * | 8/2008 | Dodo .................. | A61F 7/03 428/320.2 |
| 2008/0251062 | A1 * | 10/2008 | Dodo .................. | A61F 7/034 126/263.02 |
| 2008/0257333 | A1 * | 10/2008 | Dodo .................. | A61F 7/034 126/263.09 |
| 2008/0269850 | A1 * | 10/2008 | Dodo .................. | A61F 7/034 607/96 |
| 2008/0283036 | A1 * | 11/2008 | Dodo .................. | A61F 7/034 126/263.02 |
| 2008/0283037 | A1 * | 11/2008 | Dodo .................. | A61F 7/034 126/263.02 |
| 2008/0283038 | A1 * | 11/2008 | Dodo .................. | A61F 7/034 126/263.06 |
| 2009/0000610 | A1 * | 1/2009 | Dodo .................. | A61F 7/034 126/263.01 |
| 2009/0047596 | A1 * | 2/2009 | Felder ................. | B41M 5/42 430/200 |
| 2009/0062890 | A1 | 3/2009 | Ugajin et al. | |
| 2010/0022978 | A1 * | 1/2010 | Kasai ............... | A61F 13/15658 604/367 |
| 2010/0112454 | A1 * | 5/2010 | Visco ................. | H01B 1/122 429/246 |
| 2010/0198325 | A1 | 8/2010 | Ishikawa | |
| 2010/0255365 | A1 * | 10/2010 | Suzuta ............... | B32B 7/12 429/163 |
| 2012/0107619 | A1 * | 5/2012 | Kitagawa ............ | C08G 18/44 428/423.1 |
| 2012/0285528 | A1 * | 11/2012 | Takanohashi ......... | C08F 230/08 136/256 |
| 2013/0089731 | A1 * | 4/2013 | Imanaka .................. | B05D 7/14 428/336 |
| 2013/0196167 | A1 * | 8/2013 | Kataoka ............... | C09D 5/1618 428/469 |
| 2013/0210303 | A1 * | 8/2013 | Doi ................... | B32B 17/02 442/67 |
| 2014/0106127 | A1 * | 4/2014 | Lyons ................ | G02B 1/12 428/143 |
| 2014/0162108 | A1 * | 6/2014 | Visco ................. | H01M 4/13 429/131 |
| 2014/0291577 | A1 * | 10/2014 | Ugajin ................ | C09D 7/14 252/182.33 |
| 2014/0373828 | A1 * | 12/2014 | Oka .................. | A61F 7/034 126/263.05 |
| 2015/0184891 | A1 * | 7/2015 | Oka .................. | A61F 7/034 126/263.05 |
| 2016/0035999 | A1 * | 2/2016 | Ii .................... | H01L 51/5253 257/40 |

FOREIGN PATENT DOCUMENTS

| | | |
|---|---|---|
| JP | 9-75388 A | 3/1997 |
| JP | 10-155827 A | 6/1998 |
| JP | 11-56896 A | 3/1999 |
| JP | 2003-102761 A | 4/2003 |
| JP | 2004-143232 A | 5/2004 |
| JP | 3666356 B2 | 6/2005 |
| JP | 2006-271962 A | 10/2006 |
| JP | 2007-185396 A | 7/2007 |
| JP | 2008-200435 A | 9/2008 |
| JP | 2008-220788 A | 9/2008 |
| JP | 4155791 B2 | 9/2008 |
| JP | 2009-39370 A | 2/2009 |

(56) References Cited

FOREIGN PATENT DOCUMENTS

| JP | 2009-519753 A | 5/2009 |
| JP | 2010-131088 A | 6/2010 |
| JP | 2012-130381 A | 7/2012 |
| WO | WO 98/00077 A1 | 1/1998 |
| WO | WO 2005/011543 A1 | 2/2005 |

OTHER PUBLICATIONS

International Search Report for PCT/JP2011/063853 dated Sep. 13, 2011.

* cited by examiner

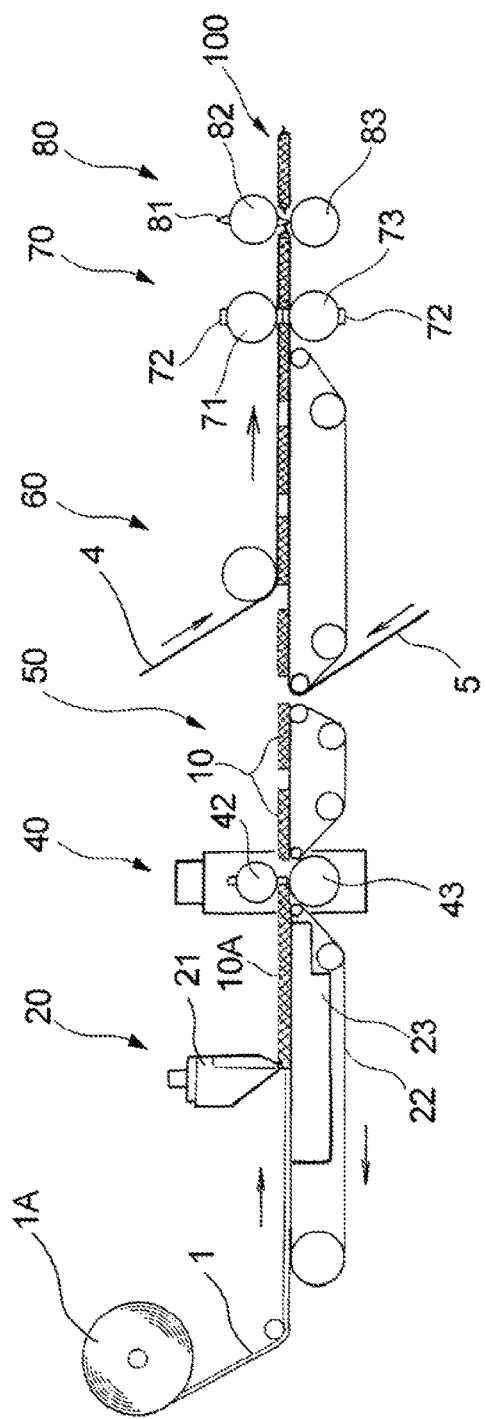
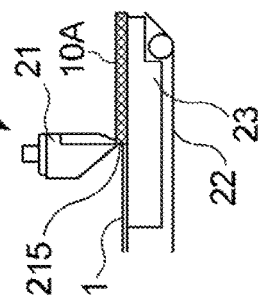
Fig. 2
Fig. 2(a)

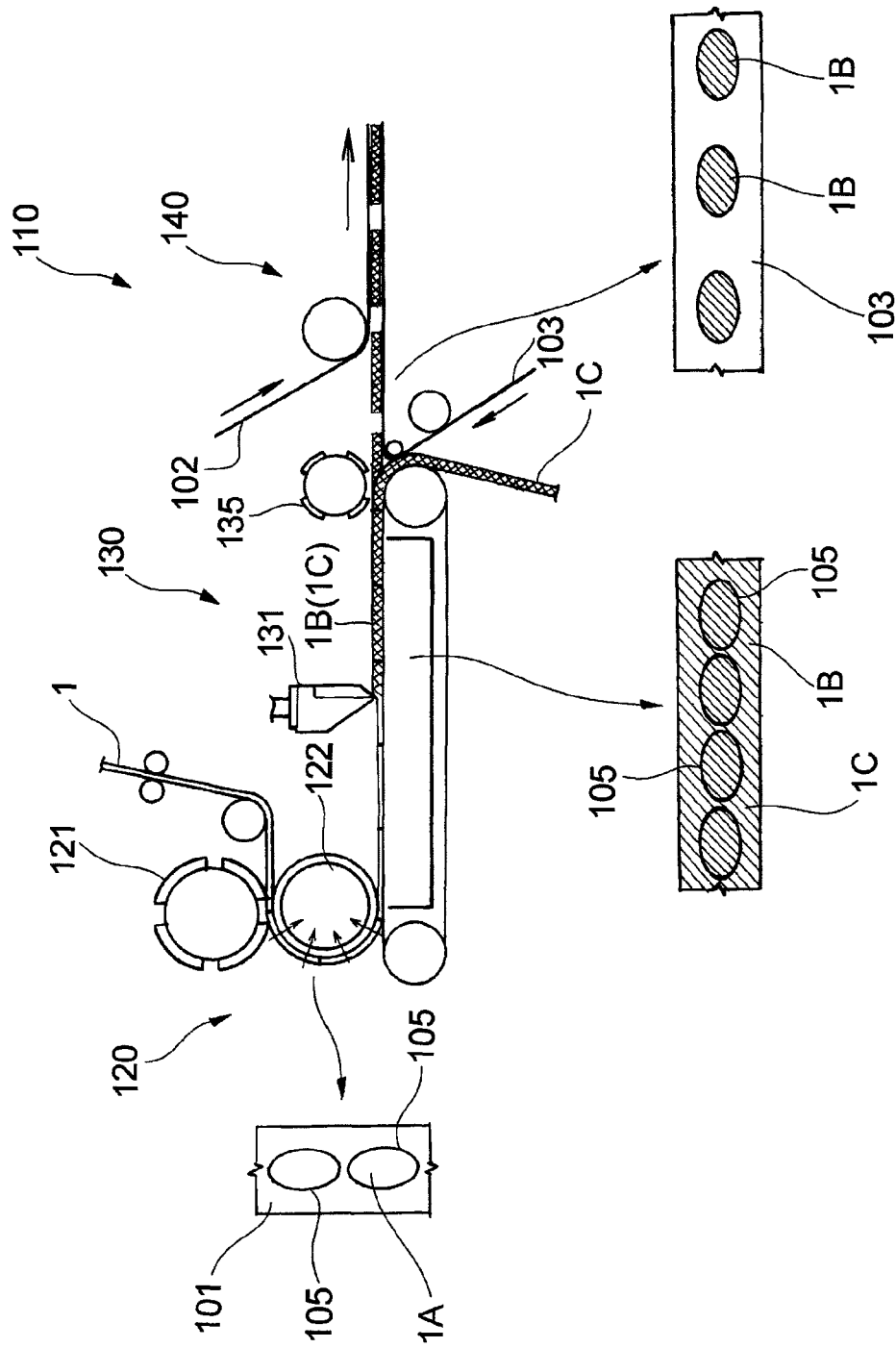

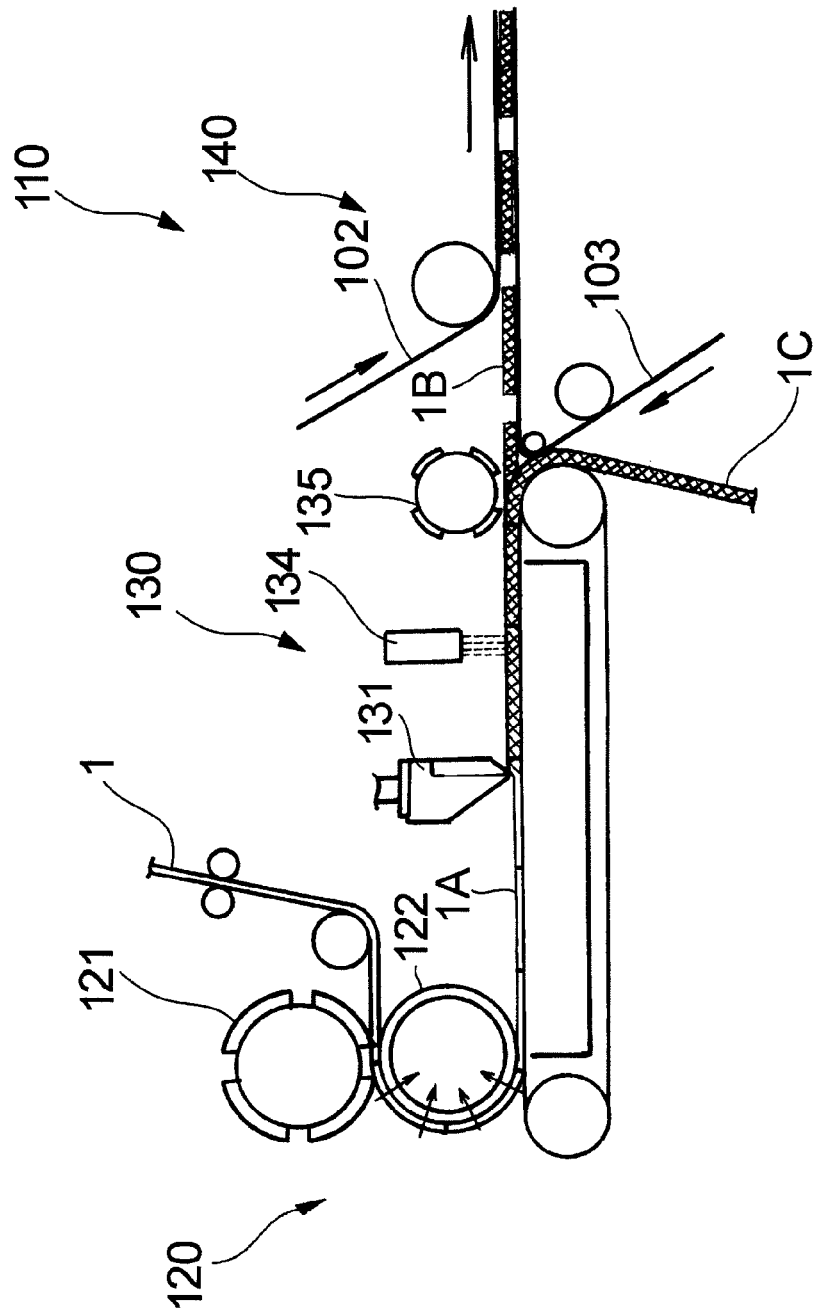

Fig. 19
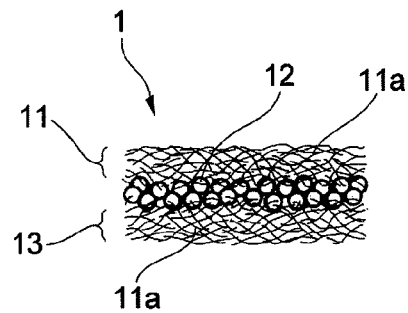
Fig. 20(a) Example 1
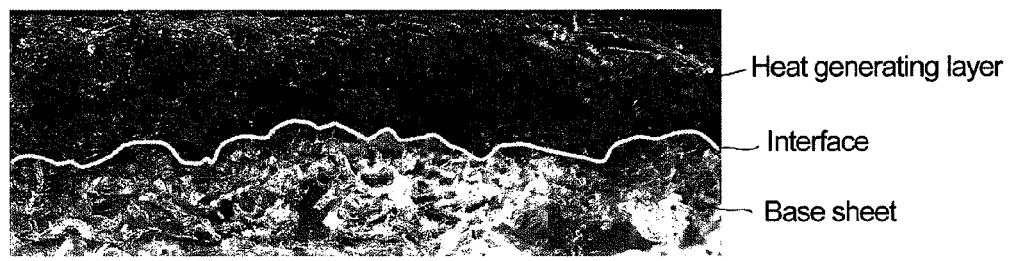
Heat generating layer
Interface
Base sheet
Fig. 20(b) Comparative Example 2
Heat generating layer
Interface
Base sheet

HEAT GENERATING DEVICE

TECHNICAL FIELD

The present invention relates to a heat generating device making use of the heat associated with oxidation of an oxidizable metal. It also relates to a method for making a heat generating element used to advantage in the heat generating device. It also relates to a method for making a sheet having a coating layer formed by applying a viscous material.

BACKGROUND ART

Techniques relating to a heat generating element constructed by uniting a heat generative composition containing an oxidizable metal and a water-absorbent sheet are known. For example, patent literature 1 below proposes a heat generating element having an ink-like or creamy heat generative composition disposed on and sealed in an enclosing material of sheet form, the enclosing material partly possessing air permeability and water absorbency, and the enclosing material having absorbed part of the water content of the ink-like or creamy heat generative composition. Excessive water, free water, and/or water-containing gel present in the heat generative composition perform a function as a barrier layer against air and prevents an exothermic (heat generating) reaction from occurring. Excess water and the like being absorbed by the enclosing material having water absorbing properties, the barrier layer disappears thereby to cause heat generation to proceed. The patent literature 1 teaches that the heat generating element disclosed is obtained by depositing, on a base sheet (an enclosing material), a layer of an ink-like or creamy heat generative composition, the heat generative composition being prepared by stirring activated carbon, a thickener, a surfactant, a pH adjuster, edible salt, and iron powder in the order described in a prescribed compounding ratio and further kneading the mixture while adding water thereto.

Apart from that technique, patent literature 2 discloses a heat generating element including a layer of a flowable viscous heat generative composition disposed on and enclosed in an enclosing material of sheet form. The heat generating element further includes an air-permeable water absorbent sheet that covers one or both sides of the heat generative composition but is absent in the sealed portion of the enclosing material. The enclosing material of sheet form partly has air permeability. The air permeable, water absorbent sheet is fixed to a predetermined portion of the heat generative composition by the adhesive force of the heat generative composition. The heat generating element is produced by applying the flowable viscous heat generative composition to the air permeable water absorbent sheet in a prescribed pattern, overlaying another water absorbent sheet thereon to cover the heat generative composition, immobilizing the two absorbent sheets by the adhesive force of the heat generative composition sandwiched in between to make a laminate, die-cutting the laminate in a shape greater than the shape of the heat generative composition and excluding the peripheral portion that will be a sealed portion (not so great as to include the peripheral portion that will be a sealed portion), sandwiching the cut laminate between a base sheet and a cover sheet, and fusion bonding the peripheral portions of the base sheet and the cover sheet to form a sealed portion.

The assignee common to this application previously disclosed in patent literature 3 below a method for producing a heat generating molded article. The method includes applying a coating fluid containing oxidizable metal powder, a fibrous material, water, and a moisture retaining agent and having a water content of 40% to 75% by mass to a support to form a water-containing molded mat, dewatering the water-containing molded mat to a prescribed water content, heat drying the dewatered water-containing molded mat to a prescribed water content to make an intermediate product, and incorporating a prescribed amount of an aqueous electrolyte solution into the resulting intermediate product to make a heat generating molded article. According to this method, since the coating fluid is free from an electrolyte, oxidation of the oxidizable metal particles is prevented from proceeding during the steps of applying the coating fluid, dewatering, and drying to make the intermediate product, and the disperse state of the heat generative composition is maintained.

Patent literature below 4 describes a heat generating sheet comprising a heat generative composition and a support, the support being formed of nonwoven fabric and supporting the heat generative composition. The heat generative composition is held in a great number of voids in the nonwoven fabric. As proposed by the literature, the heat generative composition may be held by a method including spreading a mixture of powdered raw materials, such as iron powder, activated carbon, and an inorganic electrolyte, on nonwoven fabric and vibrating the nonwoven fabric to allow the powdered raw materials to penetrate into the voids inside the nonwoven fabric.

Patent literature 5 discloses a process of producing a heat generating molded article including the steps of making an intermediate product by a papermaking process from a raw material composition containing an oxidizable metal powder, a moisture retaining agent, a fibrous material, and water and incorporating an electrolyte into the resulting intermediate product. The electrolyte can be incorporated into the intermediate product by impregnating the intermediate product with a solution of the electrolyte having a prescribed concentration or adding the electrolyte in a solid state with a prescribed particle size to the intermediate product.

CITATION LIST

Patent Literature

Patent literature 1: U.S. Pat. No. 6,436,128B1
Patent literature 2: US 2002/121624A1
Patent literature 3: JP 2004-143232A
Patent literature 4: JP 7-59809A
Patent literature 5: US 2005/0000827A1

SUMMARY OF INVENTION

Technical Problem

According to the technique of patent literature 1, a water-containing viscous heat-generative composition is laminated directly with an air permeable sheet or covers, while it is viscous, an air permeable sheet, the air permeability of the sheet is liable to be impaired due to the viscosity of the heat generative composition, which can impede a uniform exothermic reaction. Since the sheet on which a layer of the heat generative composition is formed is an enclosing material, the movement of a wearer will be transmitted directly to the layer of the heat generative composition, whereby the layer of the heat generative composition can come off easily. According to the disclosed technique, the presence of excessive water is effective in controlling heat generation during stirring and kneading in the preparation of the heat generative composition. However, because the mixture being stirred and kneaded contains edible salt (electrolyte) and iron powder as well, the composition adhering to the paddle of a kneader, the inner wall of a tank, and the like will undergo vigorous oxidation reaction on losing the water content. Therefore, the manufacturing equipment should be made from a highly anticorrosive expensive material, like titanium, which incurs high cost of equipment investment. In the preparation of the heat generative composition, because the mixture being stirred and kneaded contains edible salt (electrolyte) and iron powder as well, the resulting heat generative composition tends to suffer from settling of components or separation of water and have difficulty in retaining the disperse state of the dispersoid. Furthermore, since the heat generative composition disclosed contains a metal chloride as noted above, the composition is liable to undergo change in viscosity with time on account of the metal chloride. A viscosity change with time is one of the causes that hinder stable application of the heat generative composition.

Patent literature 2 discloses an embodiment in which the viscous heat generative composition is disposed in layer on an absorbent sheet separate from an enclosing material, another absorbent sheet is put on the layer of the heat generative composition to provide a laminate sheet having the composition between the absorbent sheets taking advantage of the viscous property of the composition, and the laminate sheet is enclosed in an enclosing material. This embodiment fails to secure sufficient air passage. In the case when the heat generative composition is designed to generate not only heat but steam, generation of steam would also be hindered. Because die-cutting is conducted after the heat generative composition is applied to the absorbent sheet to form a coating layer, the heat generative composition will adhere to the cutter blade due to its viscosity, which easily results in machine trouble and contamination of equipment. Moreover, the absorbent sheet is liable to move out of proper position when die-cut. In addition, according to the method of patent literature 2, because the heat generative composition is applied in a prescribed pattern, it is not easy with a highly viscous heat generative composition to achieve good reproducibility of a designed pattern with high productivity.

The method for making a heat generating molded article disclosed in patent literature 3, which involves the steps of dewatering and heat drying, tends to require an increased number of production steps or an increased scale of production equipment. If the dewatering step and the drying step are omitted, the heat generating element would have a sticky surface due to the water content of the coating fluid and the water content of the aqueous electrolyte solution. This can increase the burden of production equipment maintenance and, in the case when the heat generating element is covered with an air permeable enclosing material, the pores of the enclosing material might be clogged, resulting in liability of a failure to obtain desired heat generation performance.

According to the technique of patent literature 4, a mixture prepared by mixing powdered raw materials, such as iron powder, activated carbon, and an inorganic electrolyte, is spread on nonwoven fabric. However, because iron powder, activated carbon, and an inorganic electrolyte are different in particle size or shape, it is not easy to uniformly mix them and uniformly spread them.

In the technique disclosed in patent literature 5, in the case when an electrolyte in a solid state is added to an intermediate product formed by a papermaking process, it is not easy for the intermediate product to stably hold the solid electrolyte even if the intermediate product contains water. That is, the electrolyte added to the intermediate product easily falls off from the intermediate product being transported. As a result, the production equipment is apt to be contaminated, and it is not easy to ensure presence of a given amount of the electrolyte.

Accordingly, the present invention relates to a heat generating device free from the disadvantages of the aforementioned conventional techniques and a method for making a heat generating element which is used to advantage in the heat generating device.

Solution to Problem

To solve the above described problems, the inventors have conducted extensive study. They found as a result that a heat generating element obtained by forming a layer of a heat generative composition on a water-absorbing fibrous sheet has a successfully controlled water content in the layer of the heat generative composition by taking advantage of the water absorbency of the fibrous sheet. They have also found that the heat generating element is enclosable in a non-fixed state in an independent air-permeable enclosing material, thereby securing sufficient air passage and preventing the layer of the heat generative composition from falling off with the movement of a wearer.

The inventors have also found that using a fibrous sheet containing a superabsorbent polymer as a base sheet and adding oxidizable metal particles and an aqueous electrolyte solution in separate steps to make a layer of a heat generative composition, specifically first adding oxidizable metal particles and then adding an aqueous electrolyte solution, allow for maintaining the disperse state of the components in a coating material, controlling undesirable oxidation of the oxidizable metal during the production processing to provide a heat generating element exhibiting good heat generation characteristics to advantage, and providing ease of control on the water content of the heat generating layer of the heat generating element.

The invention has been completed based on the above findings. The invention solves the above problems by providing a heat generating device including a heat generating element and an enclosing material entirely enclosing the heat generating element, the heat generating element including a base sheet formed of a fibrous sheet containing superabsorbent polymer particles and hydrophilic fibers and a layer of a heat generative composition containing oxidizable metal particles located on the base sheet. The enclosing material includes a first cover sheet and a second cover sheet. The first and the second cover sheet are bonded to each other in their peripheral portions to provide a space in which the heat generating member is placed. The heat generating element is in the enclosing material in a non-fixed state. The first cover sheet has air permeability in a part thereof and is located on the side of the layer. The heat generating device is configured to release steam from the side of the first cover sheet while in use.

The invention provides the following heat generative device.

[1] A heat generating device comprising a heat generating element and an enclosing material entirely enclosing the heat generating element,
the heat generating element comprising:
a base sheet formed of a fibrous sheet containing superabsorbent polymer particles and hydrophilic fibers, and a layer of a heat generative composition containing oxidizable metal particles located on a side of the base sheet, the enclosing material comprising a first cover sheet and a second cover sheet bonded to each other in their peripheral portions to provide a space therebetween in which the heat generating member is placed, the heat generating element placed in the space being in a non-fixed state to the enclosing material, the first cover sheet having air permeability in a part thereof and being located on the side of the layer of a heat generative composition, and the heat generating device being configured to release steam from the side of the first cover sheet while in use.

The invention provides in its preferred embodiments the following structures and methods.

[2] The heat generating device as set forth in [1] above, wherein the second cover sheet has lower air permeability than the first cover sheet.

[3] The heat generating device as set forth in [1] or [2] above, wherein the layer of a heat generative composition is located on only one side of the base sheet

[4] The heat generating device as set forth in [1] or [2] above, wherein the layer of a heat generative composition is located between the base sheet and another base sheet, the two base sheets being the same or different from each other.

[5] The heat generating device as set forth in [2] above, wherein the layer of a heat generative composition is in a water-containing state.

[6] The heat generating device as set forth in any one of [1] to [5] above, wherein the hydrophilic fibers include cellulose fibers.

[7] The heat generating device as set forth in [6] above, wherein the cellulose fibers are bulky cellulose fibers.

[8] The heat generating device as set forth in [7] above, wherein the bulky cellulose fibers have (a) at least one three-dimensional structure selected from a twist, a crimp, a bend, and a branch, (b) a fiber coarseness of 0.2 mg/m or more, or (c) an intramolecular or intermolecular cross-linked structure.

[9] The heat generating device as set forth in any one of [1] to [8], wherein the base sheet is a single sheet containing the superabsorbent polymer particles predominantly in its middle portion in the thickness direction and containing substantially no superabsorbent polymer particles on surfaces thereof.

[10] The heat generating device as set forth in any one of [3] to [9] above, wherein the base sheet has, in its surface on which the layer of a heat generative composition is not provided, a lower water content than the layer of a heat generative composition.

[11] The heat generating device as set forth in any one of [1] to [10] above, wherein the heat generative composition has its lower part embedded in the base sheet.

[12] The heat generating device as set forth in any one of [1] to [11] above, showing a change of 350% or less in three-point bending load after the end of heat generation relative to that before the onset of heat generation.

The invention also provides a method for making a heat generating element that is used to advantage in the above described heat generating device. That is, the invention provides a method for making a heat generating element including a base sheet formed of a fibrous sheet containing superabsorbent polymer particles and hydrophilic fibers and a layer of a heat generative composition containing oxidizable metal particles, an electrolyte, and water located on the base sheet. The method includes steps of applying a coating material containing the oxidizable metal particles and not containing the electrolyte to a side of the base sheet, and adding an aqueous electrolyte solution containing the electrolyte to that side of the base sheet having the coating material applied thereto.

That is, the invention relates to:

[13] A method for making a heat generating element comprising:

a base sheet formed of a fibrous sheet containing superabsorbent polymer particles and hydrophilic fibers, and a layer of a heat generative composition containing oxidizable metal particles, an electrolyte, and water located on the base sheet, the method comprising steps of:

applying a coating material containing the oxidizable metal particles and not containing the electrolyte to a side of the base sheet, and adding an aqueous electrolyte solution containing the electrolyte to that side of the base sheet having the coating material applied thereto.

The invention provides in its preferred embodiments the following structures and methods.

[14] The method for making a heat generating element as set forth in [13] above, further comprising sucking the base sheet from the other side during applying the coating material or after applying the coating material and before adding the aqueous electrolyte solution.

[15] The method for making a heat generating element as set forth in [14] above, wherein the base sheet is not sucked from the other side thereof during adding the aqueous electrolyte solution, or the base sheet is sucked from the other side thereof during adding the aqueous electrolyte solution under a condition different from that of the suction conducted during the coating step or after the coating step and before the aqueous electrolyte solution addition.

[16] The method for making a heat generating element as set forth in any one of [13] to [15] above, wherein the aqueous electrolyte solution used in the electrolyte addition step contains an electrolyte in a ratio higher than the ratio of the electrolyte in the heat generating element to the sum of the electrolyte and water in the heat generating element.

[17] The method for making a heat generating element as set forth in any one of [13] to [16] above, wherein the aqueous electrolyte solution is patternwise applied to the base sheet within the region having the coating material applied.

[18] A method for making a heat generating device comprising the step of making a heat generating element by the method set forth in any one of [13] to [17] above and the step of entirely enclosing the resulting heat generating element in an enclosing material, the step of making a heat generating element being a step of making a heat generating element having the layer of a heat generative composition in a non-flowable state, the step of enclosing being a step of enclosing the heat generating element in that state in the enclosing material.

The invention also provides a method for making a heat generating element that is used to advantage in the above described heat generating device. The invention provides a method for making a heat generating element including a base sheet formed of a fibrous sheet containing superabsorbent polymer particles and hydrophilic fibers and a layer of a heat generative composition containing oxidizable metal particles, an electrolyte, and water located on the base sheet. The method includes steps of adding an aqueous electrolyte solution containing the electrolyte to a side of the base sheet and applying a coating material containing the oxidizable metal particles and not containing the electrolyte to that side of the base sheet having the aqueous electrolyte solution added thereto.

That is, the invention relates to:

[19] A method for making a heat generating element comprising:
a base sheet formed of a fibrous sheet containing superabsorbent polymer particles and hydrophilic fibers, and
a layer of a heat generative composition containing oxidizable metal particles, an electrolyte, and water located on the base sheet,
the method comprising steps of:
adding an aqueous electrolyte solution containing the electrolyte to a side of the base sheet, and
applying a coating material containing the oxidizable metal particles and not containing the electrolyte to that side of the base sheet having the aqueous electrolyte solution added thereto.

The invention provides in its preferred embodiments the following structures and methods.

[20] The method for making a heat generating element as set forth in [19] above, wherein the aqueous electrolyte solution used in the electrolyte addition step contains an electrolyte in a ratio higher than the ratio of the electrolyte in the heat generating element to the sum of the electrolyte and water in the heat generating element.

[21] The method for making a heat generating element as set forth in [20] above, wherein the aqueous electrolyte solution is added in the electrolyte addition step in an amount larger than the value obtained by multiplying a saturation capacity of the superabsorbent polymer for the aqueous electrolyte solution by the mass of the superabsorbent polymer present in the base sheet, the saturation capacity for the aqueous electrolyte solution being measured making use of JIS K7224.

[22] The method for making a heat generating element as set forth in any one of [19] to [21] above, further comprising sucking the base sheet from the other side after applying the coating material to the side of the base sheet having the aqueous electrolyte solution added thereto.

[23] A method for making a heat generating device comprising a heat generating element and an enclosing material enclosing the heat generating element. The method includes the step of making the heat generating element by the method as set forth in any one of [19] to [22] above and the step of entirely enclosing the resulting heat generating element in the enclosing material, wherein the layer of a heat generative composition is made in a non-flowable state prior to enclose the heat generating element in the enclosing material.

The invention also provides a method for making a heat generating element that is used to advantage in the above described heat generating device. The invention provides a method for making a heat generating element including a base sheet and a layer of a heat generative composition containing oxidizable metal particles, an electrolyte, and water on the base sheet. The method includes steps of adding the electrolyte in a solid state to a side of the base sheet and applying a coating material containing the oxidizable metal particles and water and not containing the electrolyte to the side of the base sheet. The steps are carried out in the named or reverse order or simultaneously.

That is, the invention relates to:

[24] A method for making a heat generating element comprising:
a base sheet, and
a layer of a heat generative composition containing oxidizable metal particles, an electrolyte, and water on the base sheet,
the method comprising steps of:
adding the electrolyte in a solid state to a side of the base sheet, and
applying a coating material containing the oxidizable metal particles and water and not containing the electrolyte to the side of the base sheet,
the steps being carried out in the named or reverse order or simultaneously.

The invention provides in its preferred embodiments the following structures and methods.

[25] The method for making a heat generating element as set forth in [24] above, wherein the base sheet has water absorbency.

[26] The method for making a heat generating element as set forth in [24] or [25] above, wherein the electrode is added in powder form.

[27] The method for making a heat generating element as set forth in any one of [24] to [26] above, wherein (1) the step of applying the coating material is followed by the step of adding the electrolyte to form the layer of a heat generative composition, (2) the step of adding the electrolyte is followed by the step of applying the coating material, or (3) the step of applying the coating material and the step of adding the electrolyte are carried out simultaneously, and the method further comprises the step of overlaying a second base sheet on the layer of the heat generative composition, the base sheet and the second base sheet being the same or different from each other.

[28] The method as set forth in [27] above, wherein the second base sheet is a fibrous sheet containing superabsorbent polymer particles.

[29] The method as set forth in any one of [24] to [28] above, wherein the base sheet is a fibrous sheet containing superabsorbent polymer particles.

[30] The method as set forth in any one of [24] to [29] above, wherein the base sheet is a fibrous sheet containing no superabsorbent polymer particles or a fibrous sheet containing superabsorbent polymer particles,
the step of applying the coating material is followed by the step of adding the electrolyte to form the heat generative composition, and
the method further includes the step of overlaying a second base sheet containing no superabsorbent polymer particles or containing superabsorbent polymer particles on the layer of the heat generative composition,
either one of the base sheet and the second base sheet containing superabsorbent polymer particles.

[31] A heat generating device comprising a heat generating element prepared by the method according to [30] above and an enclosing material enclosing the whole of the heat generating element, the enclosing material comprising a first cover sheet and a second cover sheet bonded to each other in their peripheral portions to provide a space in which the heat generating member is placed, the heat generating element being placed in the space of the enclosing material in a non-fixed state, the first cover sheet having air permeability in a part thereof and is on the side of the layer of a heat generative composition, the heat generating device being configured to release steam from the side of the first cover sheet while in use.

The invention also provides a method for making a sheet having a coating layer by applying a viscous material to a base sheet. The method includes steps of successively cutting a running continuous-length base sheet across the running direction to provide a plurality of cut base sheets, applying the viscous material to a side of the individual cut base sheets running with no spacing therebetween to form a coating layer, and increasing the distance between the running cut base sheets having the coating layer to create a spacing therebetween.

The invention also provides a method for making a sheet having a coating layer by applying a viscous material to a base sheet. The method includes steps of successively making slits of closed pattern in a running continuous-length base sheet to form a plurality of cut base sheets lined up in the running direction, applying the viscous material to a side of the slit, continuous-length base sheet to form a coating layer with the cut base sheets not being separated from the continuous-length base sheet, and successively separating the cut base sheets from the continuous-length base sheet having the coating layer to provide a plurality of cut base sheets each having the coating layer.

The invention also provides a method for making a sheet having a coating layer by applying a viscous material to a base sheet. The method includes steps of successively making slits in a running continuous-length base sheet to form a plurality of cut pieces of the base sheet lined up in the running direction, applying the viscous material to a side of the running continuous-length base sheet having the slits to form a coating layer without separating the cut pieces from the continuous-length base sheet, and separating and discarding a part of the cut pieces to leave a plurality of cut pieces of the base sheet each having the coating layer and a cutaway corresponding to the separated and discharged cut piece.

That is, the invention relates to:

[32] A method for making a sheet having a coating layer by applying a viscous material to a base sheet,
the method comprising steps of:
successively cutting a running continuous-length base sheet across the running direction to provide a plurality of cut base sheets,
applying the viscous material to a side of the individual cut base sheets running with no spacing therebetween to form a coating layer, and
increasing the distance between the running cut base sheets having the coating layer to create a spacing therebetween.

[33] A method for making a sheet having a coating layer by applying a viscous material to a base sheet,
the method comprising steps of:
successively making slits of closed pattern in a running continuous-length base sheet to form a plurality of cut base sheets lined up in the running direction,
applying the viscous material to a side of the slit, continuous-length base sheet to form a coating layer with the cut base sheets not being separated from the continuous-length base sheet, and
successively separating the cut base sheets from the continuous-length base sheet having the coating layer to provide a plurality of cut base sheets each having the coating layer.

[34] A method for making a sheet having a coating layer by applying a viscous material to a base sheet,
the method comprising steps of:
successively making slits in a running continuous-length base sheet to form a plurality of cut pieces of the base sheet lined up in the running direction,
applying the viscous material to a side of the running continuous-length base sheet having the slits to form a coating layer without separating the cut pieces from the continuous-length base sheet, and
separating and discarding a part of the cut pieces to leave a plurality of cut pieces of the base sheet each having the coating layer and a cutaway corresponding to the separated and discharged cut piece.

The invention provides in its preferred embodiments the following structures and methods.

[35] The method as set forth in any one of [32] to [34], wherein the base sheet has liquid absorbency.

[36] The method as set forth in any one of [32] to [35], wherein the viscous material is a heat generative composition containing oxidizable metal particles, an electrolyte, and water.

[37] The method as set forth in any one of [32] to [35], wherein the viscous material is a composition containing oxidizable metal particles and water and not containing an electrolyte.

[38] The method as set forth in [37] above, further comprising the step of adding an aqueous electrolyte solution to the individual cut base sheets, the individual cut pieces of the base sheet, or the slit continuous-length base sheet before the step of applying the viscous material.

[39] The method as set forth in [37] above, further comprising the step of adding an aqueous electrolyte solution to the base sheet having the viscous material applied thereto after the step of applying the viscous material.

[40] The method as set forth in [39] above, wherein the aqueous electrolyte solution is added before increasing the distance between the cut base sheets or before separating the cut base sheets or the cut pieces of the base sheet from the slit continuous-length base sheet.

[41] The method as set forth in [39] above, wherein the aqueous electrolyte solution is added after increasing the distance between the cut base sheets or after separating the cut base sheets or the cut pieces of the base sheet from the slit continuous-length base sheet.

[42] The method as set forth in any one of [32] to [41] above, further comprising the step of cutting the coating layer before increasing the distance between the cut base sheets or before separating the cut base sheets or the cut pieces of the base sheet.

Advantageous Effects of Invention

According to the invention, there is provided a heat generating device that is capable of uniform heat generation from the onset to the end of heat generation and less likely to cause the heat generative composition to fall off with the movement of a wearer. The heat generating device of the invention has flexibility even after the end of heat generation and therefore provides a good fit to the contour of the wearer's body thereby causing little discomfort to the wearer from the onset to the end of heat generation. The heat generating device of the invention achieves a good fit against a nonplanar surface of the wearer's body, such as a joint or a curved portion and therefore imparts a uniform warming sensation to the wearer.

According to the method of the invention for making a heat generating element, the components of the coating material maintain good dispersibility, and the oxidation of the oxidizable metal particles is controlled during the manufacturing processing. As a result, a heat generating element having good heat generation characteristics is produced, and it is easy to control the water content of the heat generating layer of the heat generating element. Furthermore, according to the method, when an air-permeable sheet is used as an enclosing material, the air permeability of the sheet is hardly impaired, and the layer of the heat generative composition hardly falls off. Thus, a heat generating device having excellent heat generation characteristics is provided.

According to the method of the invention for making a heat generating element, the oxidation of oxidizable metal particles by the action of the aqueous electrolyte solution is minimized, and the heat generative composition maintains the disperse state of the dispersoid. The method thus provides a heat generating element having good heat generation characteristics. In addition, the method achieves reduction of the number of steps involved or the scale of the production equipment.

According to the method of the invention for making a heat generating element, the coating material, being free from an electrolyte, has a stable viscosity and exhibits good dispersed state of the dispersoid before application. The equipment for preparing the coating material and the equipment for applying the coating material are prevented from corrosion. Because the electrolyte is added in a solid state, addition of excess water to the heat generating element is avoided, which stabilizes the processing of the heat generating element. Avoidance of adding excess water to the heat generating element is effective in preventing processing equipment from being splashed with water and preventing processing failure from occurring due to sticking of the heat generating element to the processing equipment. As a result, an improved production yield is attained. Moreover, avoidance of adding excess water to the heat generating element is effective in producing a heat generating element having stable heat generation characteristics.

According to the invention, because the base sheet is cut to prescribed shape before applying a viscous material, the cutting blade is prevented from being contaminated with the viscous material. As a result, reduction in cutting performance and rusting of the blade due to the adhesion of the viscous material to the blade are prevented, whereby the heat generating element is produced stably for an extended period of time.

BRIEF DESCRIPTION OF DRAWINGS

FIG. 2 is a schematic illustration of an example of an apparatus suitably used to produce the heat generating element or device of the invention.

FIG. 2(a) is an expanded view of coating part 20.

FIG. 16 is a schematic illustration of yet another example of an apparatus suitably used to produce the heat generating element or device of the invention.

FIG. 18 is a schematic illustration of still another example of an apparatus suitably used to produce the heat generating element or device of the invention.

FIG. 19 is a schematic longitudinal cross-section of the base sheet used in Example 1.

FIG. 20(a) is a micrograph of a longitudinal cross-section of the heat generating device obtained in Example 1, and FIG. 20(b) is a micrograph of a longitudinal cross-section of the heat generating device obtained in Comparative Example 2.

DESCRIPTION OF EMBODIMENTS

Figure 1A:
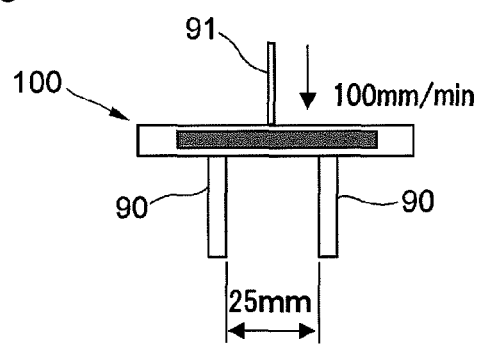
FIG. 1(a) is a side view illustrating a method for determining a three-point bending load of a heat generating device.

The invention will be shown with reference to its preferred embodiments. The heat generating device of the invention includes a heat generating element and an enclosing material as constituent members. The heat generating element is a member that generates heat in the heat generating device of the invention. The enclosing material is a member that encloses the whole of the heat generating element and defines the contour of the heat generating device of the invention. A part or the whole of the enclosing material has air permeability.

The heat generating element includes a base sheet and a layer of a heat generative composition (hereinafter also referred to as a heat generating layer) provided on a side of the base sheet. The base sheet is formed of a fibrous sheet containing particles of a superabsorbent polymer and hydrophilic fibers. The heat generating layer contains particles of an oxidizable metal.

The base sheet formed of a fibrous sheet may be (i) a single sheet in which superabsorbent polymer particles and hydrophilic fibers are uniformly mixed. The base sheet may also be (ii) a single-ply sheet containing superabsorbent polymer particles predominantly in its middle portion in the thickness direction and containing substantially no superabsorbent polymer particles on surfaces thereof. The base sheet may also be (iii) a laminate sheet composed of two hydrophilic fiber-containing fibrous sheets, which may be the same or different, and superabsorbent polymer particles disposed between the two fibrous sheets. Of the base sheets having various configurations as described, those having the configuration (ii) are preferably used to provide ease of controlling the water content of the heat generating layer.

The hydrophilic fibers contained in the base sheet formed of a fibrous sheet may be either natural fiber or synthetic fiber. By using hydrophilic fibers to construct the base sheet, the advantage is obtained that hydrogen bonds are easily formed with the oxidizable metal contained in the heat generating layer to improve the shape retention of the heat generating layer. Using hydrophilic fibers is also advantageous in that the water absorbency and water retention of the base sheet are improved to make it easier to control the water content of the heat generating layer. From these viewpoints it is preferred to use cellulose fiber as hydrophilic fiber. The cellulose fiber may be chemical (synthetic) fiber or natural fiber.

Chemical cellulose fiber may be, for example, rayon or acetate fiber. Examples of natural cellulose fiber include various plant fibers, such as wood pulp, non-wood pulp, cotton, flax, straw, hemp, jute, kapok fiber, coconut fiber, and rush. Preferred of these cellulose fibers is wood pulp in view of availability of thick fibers. To use thick fibers as cellulose fiber is advantageous in terms of water absorbency and water retention of the base sheet and ability to support the heat generating layer.

It is particularly preferred to use bulky cellulose fiber as natural cellulose fiber. To use bulky cellulose fiber makes it easier to obtain a suitable interfiber distance of the fibers making up the base sheet. Examples of the bulky cellulose fibers include (a) those having at least one three-dimensional structure selected from a twist, a crimp, a bend, and a branch, (b) those having a fiber coarseness of 0.2 mg/m or more, and (c) those having an intramolecular or intermolecular crosslinked structure.

Examples of the fibers (a) that have a three-dimensional structure selected from a twist, a crimp, a bend, and a branch include chemical pulp obtained by decomposing wood pulp through a chemical reaction, pulp obtained by disintegrating wood pulp by a mechanical treatment (beating), and pulp obtained by a combination of a chemical reaction and a mechanical treatment.

The fibers (b) are accumulated while creating bulkiness to form a base sheet in which a liquid is allowed to penetrate at an increased rate with reduced resistance. When a heat generative composition (coating material) is applied to a base sheet made up of such fibers in the production of a heat generating element as described later, the water content of the heat generative composition easily penetrates into the base sheet, making it easier to control the water content of the heat generating layer. By using such fibers, a bulky network structure capable of retaining the solid matter of the coating material that constructs the heat generating layer is easily formed. From these viewpoints, the fiber coarseness of the fibers (b) is preferably 0.2 to 2 mg/m, more preferably 0.3 to 1 mg/m.

The terminology "fiber coarseness" means a measure used to represent the thickness of fiber with uneven thickness, such as wood pulp. A fiber coarseness may be measured using, for example, a fiber length analyzer FS-200 available from Kajaani Electronics, Ltd. Examples of cellulose fiber having a fiber coarseness of 0.2 mg/m or more include Albacel (softwood kraft pulp from Federal Paper Board Co.) and Indorayon (softwood kraft pulp from PT Inti Indoraryon Utama).

The bulky cellulose fiber (b) preferably has a cross-sectional circularity of 0.5 to 1, more preferably 0.55 to 1. The bulky cellulose fiber having such a circularity allows a liquid to penetrate at a further increased rate, meeting with further reduced resistance. A cross-sectional circularity of fiber is measured as follows. A fiber is sliced in a direction perpendicular to its length, taking care to minimize the change in cross-sectional area, and the cut area is microphotographed. The micrograph is analyzed on an image analyzer (Avio EXCEL, from Nippon Avionics Co., Ltd.) to measure the circumference and the cross-sectional area of the fiber. The circularity of the fiber is calculated from formula using the measured values:

$$\text{Cross-sectional circularity} = 4\pi(\text{cross-sectional area of measured fiber})/(\text{circumference of measured fiber})^2$$

Measurements are made on randomly chosen 100 cut areas to obtain an average circularity.

In the case when wood pulp is used as bulky cellulosic fiber, wood pulp generally has a flattened cross-section as a result of delignification, having a circularity of less than 0.5 for the most part. Such flat wood pulp fibers can be converted to fibers with a circularity of 0.5 or more by mercerization (swelling). Commercially available mercerized pulps include FILTRANIER (trade name) and POROSANIER (trade name), both available from ITT Rayonier, Inc.

The crosslinked cellulose fiber (c) is preferred for its ability to retain the bulkiness even in a wet state. Crosslinking of cellulose fiber may be achieved by using a crosslinking agent. Useful crosslinking agents include N-methylol compounds, such as dimethylol ethylene urea and dimethylol dihydroxyethylene urea; polycarboxylic acids, such as citric acid, tricarballylic acid, and butanetetracarboxylic acid; polyols, such as dimethylhydroxyethylene urea; and polyglycidyl ether compounds. The amount of the crosslinking agent to be used is preferably 0.2 to 20 parts by mass per 100 parts by mass of the cellulose fiber. The crosslinked cellulose fiber preferably has a fiber coarseness of 0.1 to 2 mg/m, more preferably 0.2 to 1 mg/m. The crosslinked cellulose fiber preferably has a cross-sectional circularity of 0.5 to 1, more preferably 0.55 to 1. Commercially available crosslinked cellulose fibers include High Bulk Additive from Weyerhaeuser Paper Co. In the following description, all the parts are by mass.

To use the fibers (c) inter alia out of the fibers (a) to (c) provides the following advantages. The base sheet achieves high integrity with a heat generating layer so that the heat generating layer hardly falls off. The resulting heat generating element is flexible and fits better to an object to which it is applied, for example, the skin or the garment of a wearer. It is noteworthy that the heat generating element surprisingly retains its flexibility even after the end of heat generation.

The hydrophilic fiber preferably has a fiber length of 0.5 to 6 mm, more preferably 0.8 to 4 mm, to secure ease of making the base sheet in a dry or wet process.

If desired, the base sheet may contain heat-fusible fiber in addition to the hydrophilic fiber to have increased strength in a wet state. The amount of the heat fusible fiber to be used is preferably 0.1% to 10% by mass, more preferably 0.5% to 5% by mass, based on the total mass of the fibers present in the base sheet.

As earlier described, the base sheet formed of a fibrous sheet contains superabsorbent polymer particles. The location of the superabsorbent polymer particles in the base sheet is as discussed above. It is preferred to use, as a superabsorbent polymer, a hydrogel material capable of absorbing and retaining 20 or more times its own weight of a liquid, and turning into a gel. The particles may have spherical, lumpy, aciniform, fibrous, or other shapes and preferably have a particle size of 1 to 1000 µm, more preferably 10 to 500 µm. Examples of the superabsorbent polymer include starch, crosslinked carboxymethyl cellulose, polyacrylic acid and salts thereof, such as homopolymers or copolymers of acrylic acid or an alkali metal salt thereof, and polyacrylic acid salt graft polymers. The superabsorbent polymer particles are preferably bonded to the fibrous material of the base sheet. The bonding may be achieved by, for example, making use of the tackiness developed by wetting the superabsorbent polymer particles. Otherwise, the bonding may be achieved by applying a liquid containing a polymerizable monomer and/or a prepolymer of the monomer to a web of the fibrous material and causing the monomer and/or the prepolymer to polymerize in situ to form superabsorbent polymer particles bonded to the fibrous material.

The proportion of the superabsorbent polymer particles in the base sheet is preferably 10% to 70% by mass, more preferably 20% to 55% by mass, from the standpoint of obtaining appropriate water absorbency and retentivity and ease of control on the water content of the heat generating layer. The proportion recited is a value measured for a base sheet in dry state before the formation of a heat generating layer thereon.

The base sheet preferably has a basis weight of 10 to 200 g/m$^2$, more preferably 35 to 150 g/m$^2$. The base sheet having a basis weight in that range exhibits sufficient wet strength and appropriate water absorbency and retentivity. The amount of the superabsorbent polymer in the base sheet is preferably 5 to 150 g/m$^2$, more preferably 10 to 100 g/m$^2$. Presence of that amount of the superabsorbent polymer further ensures appropriate water absorbency and retentivity of the base sheet and provides more ease of control on the water content of the heat generating layer. The amount of the superabsorbent polymer recited is a value measured for a base sheet in dry state before the formation of a heat generating layer thereon.

A base sheet having the configuration (i) described above may be prepared by, for example, an airlaying process. A base sheet having the configuration (ii) may be prepared by, for example, a wet papermaking process as described in commonly assigned JP 8-246395A. A base sheet having the configuration (iii) may be prepared by, for example, an airlaying process or a wet papermaking process.

The base sheet has a heat generating layer on at least one side thereof. The heat generating layer may be provided on either or both of the two sides of the base sheet. Otherwise, the heat generating layer may be provided between two base sheets that may be the same or different. When provided between two base sheets, the heat generating layer is effectively prevented from sticking to the enclosing material. When the heat generating layer is sandwiched in between two base sheets, either of the base sheets does not need to contain superabsorbent polymer particles. The heat generating layer is a water-containing layer containing oxidizable metal particles, an electrolyte, and water. The heat generating layer may further contain a reaction accelerator. The heat generating layer may be on the base sheet or may have its lower part embedded in the base sheet. The heat generating layer preferably has its lower part embedded in the base sheet. To put it another way, it is preferred that part of the solid matter constructing the heat generating layer be held in the three-dimensional network of the fibrous sheet forming the base sheet. Having part of the heat generating layer embedded in the base sheet increases the unity of the heat generating layer and the base sheet and effectively prevents the heat generating layer from coming off the base sheet before, during, and after use.

Examples of the oxidizable metal contained in the heat generating layer include iron, aluminum, zinc, manganese, magnesium, and calcium. The oxidizable metal particles may have a particle size of, e.g., about 0.1 to 300 µm. The reaction accelerator is preferably chosen from substances that act as a moisture retaining agent and also function as an oxygen retentive supplier for the oxidizable metal. Examples of the reaction accelerator include activated carbon (e.g., coconut shell activated carbon, wood activated carbon, bituminous coal, peat, and lignite), carbon black, acetylene black, graphite, zeolite, pearlite, vermiculite, and silica. The electrolyte is chosen from those substances capable of dissolving an oxide film formed on the surface of oxidizable metal particles. Examples of such electrolytes include sulfates, carbonates, chlorides, and hydroxides of alkali metals, alkaline earth metals or transition metals. Preferred of them are chlorides of alkali metals, alkaline earth metals or transition metals for their electrical conductivity, chemical stability, and production cost. In particular, sodium chloride, potassium chloride, calcium chloride, magnesium chloride, iron (I) chloride, and iron (II) chloride are more preferred.

Provided that the base sheet has the above recited basis weight, the amount of the oxidizable metal in the heat generating element is preferably 100 to 3,000 g/m$^2$, more preferably 200 to 1,500 g/m$^2$, to secure a sufficient heat value. The amount of the reaction accelerator in the heat generating element is preferably 4 to 300 g/m$^2$, more preferably 4 to 80 g/m$^2$, even more preferably 8 to 50 g/m$^2$, to secure continuation of stable heat generation for an extended period of time. The amount of the electrolyte in the heat generating element is preferably 4 to 80 g/m$^2$, more preferably 4 to 40 g/m$^2$, even more preferably 5 to 30 g/m$^2$ for the same purpose. The above recited amounts are per side of the base sheet. When the heat generating layer is formed on both sides of the base sheet, the amounts double. These amounts are adjusted as appropriate to the intended use of the heat generating element.

As noted above, the heat generating layer contains water. The water content of the heat generating layer is preferably 5% to 50%, more preferably 6% to 40%, by mass. With the water content being within that range, the heat generating layer has low flowability and low viscosity. Thus, placing an air permeable sheet on the upper side of the heat generating layer is less likely to cause the inconvenience that the heat generating layer sticks to the sheet to impair the air permeability of the sheet. The water content of the heat generating layer as discussed herein is a value measured for the portion of the heat generating layer above the surface of the base sheet. The portion of the heat generating layer embedded in the base sheet is excluded from the object of water content measurement. The water content of the heat generating layer is measured as follows. The part of the heat generating layer located above the surface of the base sheet is taken out in a nitrogen atmosphere and weighed. The heat generating layer is then freed of water in a drying oven at 105° C. in vacuo for 2 hours and weighed again to calculate the water content. The water content as referred to herein is a value per single heat generating layer.

While adjusting the water content of the heat generating layer within the range recited is effective in preventing the heat generating layer from sticking to an air permeable sheet disposed thereon, there might arise a concern that the reduced water content in the heat generating layer can result in reduced heat generation characteristics. In the invention, nevertheless, the heat generation characteristics do not reduce because the base sheet contains water which will be supplied to the heat generating layer during heat generation. In particular, the base sheet contains the superabsorbent polymer, and the release of water from the superabsorbent polymer is slow. Therefore, the heat generating layer keeps on generating heat in a stable manner for a prolonged period of time. For these considerations, the proportion of water in the heat generating element, namely the water content of the heat generating element is preferably 10% to 60%, more preferably 12% to 50%, even more preferably 12% to 40%, by mass. The water content of the heat generating element is measured as follows. The heat generating element is weighed in a nitrogen environment, dried in a drying oven at 105° C. in vacuo for 2 hours to be freed of water, and weighed again. The change in mass, which corresponds to the amount of water, is divided by the mass of the heat generating element before drying, and the quotient is multiplied by 100 to give a water content. The above discussed water content of the heat generating element is a value obtained in the case where the base sheet has a heat generating layer on either one of its two sides. When the heat generating layer is formed on both sides of the base sheet, it is preferred that each heat generating layer satisfy the above recited range of water content.

From the standpoint of achieving uniform heat generation, it is preferred that water be distributed uniformly throughout the heat generating element (in both the planar direction and the thickness direction). However, the heat generating element may have a high water content portion and a low water content portion arranged in a planar direction. For example, the heat generating element may alternate a high water content portion and a low water content portion in stripes extending in one planar direction thereof. In this case, the heat generating element may be designed to have stiffness varied between the high and the low water content portion. As a result, the fit of the heat generating device is further improved when attached to, for example, the skin or the garment of a wearer for the following reason. As the oxidation reaction of the heat generating element proceeds, the heat generating element increases in hardness. The oxidation reaction stops earlier in the low water content portion than in the high water content portion so that the low water content portion does not become so hard. On the other hand, the oxidation reaction continues in the high water content portion so that the high water content portion becomes hard correspondingly. From this viewpoint, the water content in the high water content portion is preferably 20% to 60%, more preferably 25% to 50%, by mass. The water content in the low water content portion is preferably 10% to 40%, more preferably 10% to 30%, by mass, provided that it is lower than that of the high water content portion.

The heat generating element having a high and a low water content region arranged in a planar direction is preferably made by a method including applying a coating material to a wide area of a base sheet in the coating step shown in FIGS. 5 and 6 (hereinafter described) and patternwise spreading an aqueous electrolyte solution within the area coated with the coating material in the subsequent electrolyte addition step. Patterns of the patternwise spreading include stripes, lattices, staggered grids, and dots. The individual dots of a dot pattern may have circular, rhombic, oval, rectangular, triangular, or other shapes in a plan view. To form a high and a low water content portion by patternwise spreading an aqueous electrolyte solution provides not only the above described advantage resulting from the portion-to-portion difference in stiffness but also the following advantage. Because the heat generation temperature varies from portion to portion, a single heat generating element may be configured to impart a warming sensation tailored to the different parts of the wearer's body, for example, a part demanding a sufficient warming temperature and a sensitive part of the body to which a mild heating temperature is desirable. The reason why portions different in stiffness are provided is that the portion on which the electrolyte has been spread becomes harder as the oxidation reaction proceeds, whereas the portion having no electrolyte spread thereon and thereby having a lower water content stops the oxidation reaction earlier and therefore remains softer than the portion where the heat generation further continues.

Arranging a high and a low water content portion in a planar direction of the heat generating element may also be accomplished by a method in which a coating material is applied to a base sheet in a pattern such that the coating weight or water content may vary from portion to portion in a planar direction in the coating step shown in FIGS. 5 and 6 (hereinafter described), and an aqueous electrolyte solution is spread over the area of the base sheet coated with the coating material in the subsequent electrolyte addition step. The patternwise application of the coating material and the patternwise addition of the electrolyte may be used in combination.

In the case where the heat generating element has a heat generating layer on only one side of the base sheet, it is preferred that the water content in the side of the base sheet having no heat generating element provided be lower than that of the heat generating layer. By this design, the side of the base sheet having the heat generating layer functions to supply water for heat generation to the heat generating layer, and the opposite side having no heat generating layer serves to prevent adhesion of the base sheet to the cover sheet thereby causing little hindrance to air passage through the heat generating device. Such a water content relationship is advantageously established by, for example, using a base sheet having the configuration (ii) or (iii) described supra. Since the base sheet having the configuration (ii) or (iii) has the superabsorbent polymer particles localized in its middle portion in the thickness direction, after a heat generating layer is formed on one side of the base sheet, wicking of water through the base sheet is blocked in the portion where the superabsorbent polymer particles are localized. As a result, the water content in the opposite side of the base sheet is kept low.

The water content of the side having no heat generating layer is measured as follows. A layer is taken apart from the side having no heat generating layer in a nitrogen environment and weighed. The layer is then dried in a drying oven at 105° C. in vacuo for 2 hours to be freed of water and weighed again. The change in mass, which corresponds to the amount of water, is divided by the mass of the heat generating element before drying, and the quotient is multiplied by 100 to give a water content.

As previously mentioned, the heat generating device of the invention has the heat generating element enclosed in an enclosing material. The enclosing material includes a first cover sheet and a second cover sheet. The first cover sheet is disposed on the side of the heat generating element having the heat generating layer provided. The second cover sheet is disposed on the side of the heat generating element having no heat generating layer (in the case where the heat generating device has a single base sheet and a heat generating layer on only one side of the base sheet) or on the side of another heat generating layer (in the case where the heat generating device has a single base sheet and a heat generating layer on both sides of the base sheet).

The first and the second cover sheet each have an extended portion extending outward from the perimeter of the heat generating element. The extended portion of the first cover sheet and that of the second cover sheet are bonded to each other. The bonding is preferably hermetic bonding, providing a closed bonded portion continuously surrounding the heat generating element. The enclosing material formed by bonding the two cover sheets has a space in the inside in which the heat generating element is enclosed. When the bonding of the extended portions is hermetic bonding to form a closed, continuous bonded portion, fall-off of the solid matter (e.g., oxidizable metal particles) from the heat generating element enclosed in the enclosing material is certainly prevented.

The heat generating element enclosed in the enclosing material is non-fixed to the enclosing material. That is, the heat generating element is allowed to move independently of the enclosing material, not being restrained by the enclosing material. Therefore, when a pressure-sensitive adhesive is applied to the second cover sheet of the enclosing material to form a pressure sensitive adhesive layer, via which the heat generating device of the invention is attached to, e.g., the skin of a wearer, even if the second cover sheet tightens with the wearer's motion, the tightening is not transmitted to the heat generating element. Therefore, the solid matter (e.g., oxidizable metal particles) is effectively prevented from falling off the heat generating element. Not restrained and capable of moving independently of the enclosing material, the heat generating element is less likely to come into intimate contact with the cover sheet. The air passage through the cover sheet is therefore not inhibited, and the air flow inside the enclosing material and around the base sheet is not blocked. As a result, a good exothermic reaction occurs. Thus, according to the invention, heat generation of the heat generating element proceeds uniformly so that the hardening of the heat generating element associated with the heat generation also proceeds uniformly. It follows that the heat generating device of the invention hardly loses flexibility even after the end of heat generation and maintains a good fit to the wearer's body from the onset to the end of heat generation. In particular, the heat generating device of the invention successfully provides a good fit even against a non-planar body part, such as a joint or a curved portion.

Figure 1B:
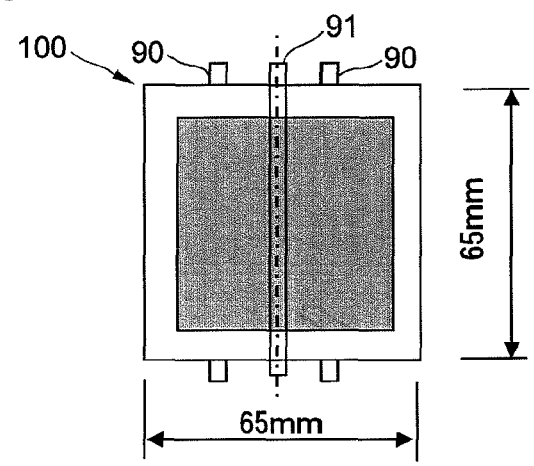
FIG. 1(b) is a plan view illustrating a method for determining a three-point bending load of a heat generating device.

The flexibility of the heat generating device of the invention can be evaluated from a three-point bending load. A smaller three-point bending load is regarded to indicate higher flexibility of the heat generating device. Measurement of a three-point bending load is carried out as follows. A tensilon universal tester (RTA-500, from Orientec Co., Ltd.) is used as a testing instrument. A heat generating device to be tested is a 65 mm-side square. As shown in FIG. 1, the heat generating device 100 is set to straddle a pair of 6 mm-wide plate-shaped supports 90 spaced away by 25 mm. The supports 90 are longer than the length of the heat generating device 100. A plate-shaped indenter 91 having a width of 1.5 mm and a length longer than the length of the heat generating device 100 is lowered from above the heat generating device 100 straddling the supports 90 at a descending speed of 100 mm/min to press the heat generating device 100 downward along a centerline between the two supports 90 until it reaches 15 mm below the supports 90. The maximum load recorded during the descending movement of the indenter 91 is taken as a three point bending load. In the invention, the three point bending load thus measured is preferably 0 to 1.5 N/65 mm, more preferably 0 to 1.0 N/65 mm, before the onset of heat generation and preferably 0.01 to 1.8 N/65 mm, more preferably 0.1 to 1.5 N/65 mm, after the end of heat generation. The ratio of change of the three point bending load after the end of heat generation to that before the onset of the heat generation is preferably 350% or less, more preferably 330% or less. This ratio of change is defined to be $[(L2-L1)/L1] \times 100$, wherein L1 is a three point bending load before the onset of heat generation, and L2 is a three point bending load after the end of the heat generation. The term "after the end of heat generation" as used herein refers to the point of time when the temperature of the heat generating element falls to 42° C. or lower.

The first cover sheet of the enclosing material has air permeability in a part of or the entire area thereof. Since the first cover sheet having air permeability is disposed facing the heat generating layer of the heat generating element as described above, oxygen is smoothly supplied to the heat generating layer, and heat generation is sustained for a long period of time. From this viewpoint, the air permeability (as measured in accordance with JIS P8117 using a B type densometer, hereinafter the same) of the first cover sheet is preferably 1 to 50,000 s/(100 ml·6.42 cm$^2$), more preferably 10 to 40,000 s/(100 ml·6.42 cm$^2$). The first cover sheet having such an air permeability is preferably, for example, a porous synthetic resin sheet permeable to moisture but impermeable to water. In using such a porous sheet, the porous sheet may be laminated on its outer side (the side of the first cover sheet facing outward) with a fiber sheet of various kinds, including nonwovens, such as needle-punched nonwoven fabric and air-through nonwoven fabric to have improved hand.

The second cover sheet of the enclosing material is selected as appropriate to the structure of the heat generating element. It is preferred for the second cover sheet to be less air-permeable than the first cover sheet so that steam may generate stably through the first cover sheet. It is preferred for the second cover sheet to be less air permeable than the first cover sheet particularly when the base sheet does not have a heat generating layer on the second cover sheet side thereof. The phrase "less air-permeable" as used herein is intended to mean "air permeable" in part but with the air permeability being lower than that of the first cover sheet or "air-impermeable". In the case of using an air impermeable sheet as the second cover sheet, the air impermeable sheet may be, for example, a synthetic resin film or a composite sheet composed of a synthetic resin film laminated on its outer side (the side facing outward) with a fiber sheet of various kinds, including nonwovens, such as needle-punched nonwoven fabric and air-through nonwoven fabric. In the case of using an air permeable sheet as the second cover sheet, the same sheet as the first cover sheet may be used. In this case, the air permeability of the second cover sheet is preferably 200 to 150,000 s/(100 ml·6.42 cm$^2$), more preferably 300 to 100,000 s/(100 ml·6.42 cm$^2$), provided that it is lower than that of the first cover sheet. To use an air permeable second cover sheet ensures stable heat generation even when the outer side of the first cover sheet is in an intimate contact with, for example, the skin or the garment of a wearer.

The heat generating element may have the heat generating layer on only one side or both sides of a single base sheet. Forming the heat generating layer on both sides of a base sheet may be achieved by, for example, applying a coating material to one side of a base sheet as described later, reversing the upper and the lower side of the coated base sheet by means of a turn bar and the like, and applying a second coating material to the other side of the base sheet. The heat generating device may have one heat generating element or two or more heat generating elements stacked one on top of another to make a multilayer structure.

The heat generating device of the invention is configured to generate steam from the side of the first cover sheet. Methods enabling steam generation include, (A) on the condition that the heat generating layer contains a large amount of water, (B) adjusting the ratio of the components making up the heat generating layer, (C) adjusting the air permeability of the first and the second cover sheet enclosing the heat generating element, and (D) a combination of the methods (B) and (C). The heat generating device of the invention is able to retain a large quantity of water because the base sheet contains hydrophilic fibers. Therefore, the heat generating device of the invention is capable of generating a large amount of steam. Moreover, the base sheet contains a superabsorbent polymer as well as the hydrophilic fibers. This ensures the capability of the base sheet to retain a large amount of water and allows for generating a large amount of steam. With respect to the method (B), adjustment of the ratio of the components making up the heat generating layer is carried out as previously discussed. With respect to the method (C), too, adjustment of the air permeability of the first and the second cover sheet is conducted as previously discussed. The amount of steam released through the first cover sheet is preferably 0.01 to 0.8 mg/(cm$^2$·min), more preferably 0.03 to 0.4 mg/(cm$^2$·min), as measured by the method described later.

In the case when both the first and the second cover sheet have air permeability, it is preferred that the first cover sheet have a smaller air permeability (i.e., higher air permeability) than the second cover sheet so that the steam generated may be released through the first cover sheet more than through the second cover sheet. As long as the steam is released through the first cover sheet more than through the second cover sheet, it is no problem that steam is released through the second cover sheet.

The amount of steam released through the first cover sheet of the heat generating device of the invention is measured as follows. A heat generating device is brought into contact with air to start heat generation in an environment of 20° C. and 65% RH. The heat generating device is put on an even balance capable of measuring in milligram unit, and the mass is measured over a period of 15 minutes. The amount of steam generated is calculated according to equation:

$$\text{Amount of steam generated [mg/(cm}^2\cdot\text{min)]} = \{(Wt_o - Wt_{15}) \times 1000\}/15S$$

wherein $Wt_0$ is the mass (g) at the start of measurement; $Wt_{15}$ is the mass (g) after 15 minutes; and S is the area of heat generating device where steam is generated.

A pressure-sensitive adhesive may be applied to the outer surface of the first cover sheet of the enclosing material to form a pressure-sensitive adhesive layer. The pressure sensitive adhesive layer is used to attach the heat generating device of the invention to the skin, the garment, and the like of a wearer. The pressure sensitive adhesive forming the pressure sensitive adhesive layer may be any of those having been used in the art, typified by hot melt pressure sensitive adhesives. The pressure sensitive adhesive layer is preferably provided on the peripheral portion of the first cover sheet so as not to block air passage.

A method suitable for making the heat generating device of the invention (hereinafter referred to as method 1) will be described. The method 1 includes (1-1) a first step (coating step) of applying a coating material which is a heat generative composition to a base sheet to prepare a heat generating element and (1-2) a second step (covering and sealing step) of enclosing the heat generating element in an enclosing material to give a heat generating device.

(1-1) Coating Step

The coating material used in the first step contains oxidizable metal particles, a reaction accelerator, an electrolyte, and water. The coating material may contain a thickener or a surfactant to increase dispersibility of the solid matter. The coating material containing these components is applied continuously on one side of, for example, a continuous-length base sheet by various coating techniques. Any known coating technique may be used, such as roller coating, die coating, screen printing, gravure coating, knife coating, or contour coating. Die coating is preferred in view of ease of coating, ease of controlling the coating build-up, and uniform application of the coating material. The details of the technique of applying a coating material using a die coater are described, e.g., in Japanese Patent 4155791.

As a result of applying the coating material, there is formed a heat generating layer continuous over one side of the base sheet. Since the base sheet contains superabsorbent polymer particles, water in the coating material is absorbed and retained by the superabsorbent polymer to a moderate degree so that the water content of the heat generating layer becomes lower than that of the coating material. As a result, the heat generating layer reduces in flowability or, preferably, loses flowability. The fact that the base sheet contains hydrophilic fibers also ensures that the water of the coating material is moderately absorbed and retained by the base sheet to reduce the water content of the heat generating layer.

In the case of forming a heat generating layer on both sides of a base sheet, a first heat generating layer is continuously formed on one side of the base sheet, and a second heat generating layer is continuously formed on the other side using a die coater, etc., either after or simultaneously with the formation of the first heat generating layer.

The coating material for the formation of a heat generating layer preferably contains 1 to 20 parts, more preferably 2 to 14 parts, of a reaction accelerator; 0.5 to 15 parts, more preferably 1 to 10 parts, of an electrolyte; 30 to 90 parts, more preferably 40 to 80 parts, of water; 0.05 to 10 parts, more preferably 0.1 to 5 parts, of a thickener; and 0.1 to 15 parts, more preferably 0.2 to 10 parts, of a surfactant each per 100 parts of oxidizable metal particles. Water is preferably present in an amount of 20% to 50%, more preferably 25% to 45%, by mass taking the total mass of the coating material as 100%. The viscosity of the coating material at 23° C. and 50% RH is preferably 500 to 30,000 Pa·s, more preferably 500 to 20,000 mPa·s, even more preferably 1,000 to 15,000 mPa·s, most preferably 1,000 to 10,000 mPa·s. The viscosity was measured with a Brookfield viscometer equipped with a No. 4 rotor at a rotor speed of 6 rpm. The coating weight of the coating material is preferably 150 to 5,000 g/m$^2$, more preferably 300 to 2,500 g/m$^2$.

(1-2) Step of Covering and Sealing Heat Generating Element (Enclosing Step)

After a continuous-length heat generating element is obtained by the above described operation, the heat generating element is covered with an enclosing material in the second step. Prior to the covering operation, it is preferred that the continuous-length heat generating element be cut across its length into individual heat generating elements. The individual heat generating elements are transported in one direction with a prescribed spacing between them. A continuous-length first cover sheet is overlaid on the heat generating layer side of the running heat generating elements, and a continuous-length second cover sheet is applied to the other side of the heat generating elements. The extended portion of the first cover sheet and the extended portion of the second cover sheet, which extend outward from the individual heat generating elements, are bonded together by a prescribed means. The bonding is performed outside the opposite lengthwise edges and the opposite transverse edges of the heat generating element by, for example, fusion bonding, ultrasonic bonding, or adhesion with an adhesive.

Because the heat generating layer has a reduced water content to have reduced or preferably no flowability by the time when the first cover sheet is overlaid on the heat generating layer, the problem of the heat generating layer sticking to the first cover sheet is avoided. As a result, the air permeability of the first cover sheet is successfully maintained.

A continuous form having a plurality of heat generating devices unidirectionally connected in series is thus obtained. The continuous form is cut across the length between adjacent heat generating devices to yield desired heat generating devices. The resulting heat generating device is sealed in an oxygen-barrier package in the subsequent step.

If desired in carrying out the method 1, any means for maintaining the production line in a non-oxidative atmosphere may be used so as to inhibit oxidation of the oxidizable metal during the production steps including the preparation of the coating material.

Two different coating materials may be used in the method 1. The two coating materials may be a high water content coating material for forming the high water content portion described supra and a low water content coating material for forming the low water content portion described supra. These coating materials are stored in different tanks and kept from mixing together until application to the base sheet. The coating materials may be applied using, for example, a coater head having two slot dies, one for the high water content coating material and the other for the low water content coating material. Otherwise, an applicator for applying a high water content coating material and another applicator for applying a low water content coating material may be used to apply the respective coating materials to the base sheet alternately in the transverse direction to form alternate stripes of high water content portions and low water content portions extending in one planar direction of the heat generating element.

In a modification of the method 1, a heat generative element having alternate stripes of high water content portions and low water content portions extending in one planar direction of the heat generating element may be obtained by applying a coating material on one side of the base sheet and applying water to prescribed portions of the coating layer to increase the water content of that portions.

The thus produced heat generating device of the invention is used to warm a human body as attached directly to the skin or to a garment of a user. Examples of human body parts to which the heat generating device is applied to advantage include shoulders, the neck, the face, eyes, hips, elbows, knees, thighs, lower legs, the abdomen, lower abdomen, hands, and soles. The heat generating device of the invention is also suited to warm or keep-warm various articles. The heat generating element made by the method 1 is useful in not only the heat generating device of the invention but otherwise configured heat generating devices and other applications. When used to warm a human body, the heat generating device of the invention is applied with its first cover sheet side, where steam generates, facing the skin (human body). The above discussed usage of the heat generating element also applies to the heat generating elements made by methods 2 to 5 hereinafter described. That is, the heat generating elements made by methods 2 to 5 are applicable to not only the heat generating device of the invention but otherwise configured heat generating devices and other applications.

FIG. 2 illustrates an example of an apparatus preferably used to carry out the method 1. The apparatus includes a coating part 20 where a coating material which is a heat generative composition is applied, a first cutting part 40, a re-pitching part 50, a covering part 60, a sealing part 70, and a second cutting part 80.

The coating part 20 has a die coater 21, an endless belt 22 formed of wire mesh that faces the die lips of the die coater 21 and runs in the direction indicated by the arrow, and a suction box 23 that faces the die lips of the die coater 21 across the endless belt 22. A continuous-length base sheet 1 unrolled from a stock roll 1A is transported by the endless belt 22, and a coating material which is a heat generative composition (215) (see FIG. 2(a)) is applied to one side of the base sheet 1 with the die coater 21 to form a heat generating layer. While the base sheet 1 is transported by the endless belt 22, the suction box 23 operates to stabilize the transportation and suck the coating material to settle the coating material on the base sheet 1. After the coating material is applied, water in the coating material is absorbed by the base sheet so that the water content of the heat generating layer is lower than that of the coating material. It follows that the heat generating layer reduces in flowability.

The thus formed continuous-length heat generating element 10A is cut in the transverse direction in the first cutting part 40. The first cutting part 40 includes a rotary die cutter 42 and an anvil roller 43, between which the heat generating element 10A passes and is cut into individual heat generating elements 10.

The cutting of the continuous-length heat generating element 10A is done in the transverse direction of the heat generating element 10A. For example, the cutting line may be straight across the heat generating element 10A, or the cutting line may be curved. In either case, while the cutting pattern is preferably such that does not produce waste trimmings, the heat generating element 10A may be cut into a desired shape, such as an oval shape or a streamlined shape.

The running pitch of the individual heat generating elements 10 is changed in the re-pitching part 50 so that they may be transported at a given spacing therebetween. Any conventionally known re-pitching mechanism can be used.

The re-pitched heat generating elements 10 are forwarded to the covering part 60, where the entire surface of the individual heat generating elements 10 is covered with a continuous-length first cover sheet 4 and a continuous-length second cover sheet 5. The first cover sheet 4 covers the side of the heat generating element 10 having the heat generating layer formed, while the second cover sheet 5 covers the other side having no heat generating layer formed. The heat generating element 10 as is covered on both sides thereof is introduced into the sealing part 70. The sealing part 70 includes a first roller 71 having a sealing projection 72 and a second roller 73 having a sealing projection 72. The two rollers 71, 73 are disposed with their axes parallel and the sealing projections 72 of the rollers 71 and 73 in contact with each other or close to each other with a prescribed clearance. In the sealing part 70, the extended portions of the first sheet 4 and the second sheet 5 extending outward from the lengthwise edges and transverse edges of the heat generating element 10 are bonded by heat sealing. The bond thus formed is a hermetic bond continuously surrounding the heat generating element 10 or a bond discontinuously surrounding the heat generating element 10.

Figure 3:
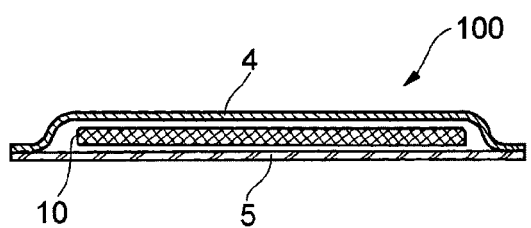
FIG. 3 is a schematic longitudinal cross-section of an embodiment of the heat generating device of the invention.

There is obtained a continuous form of a plurality of heat generating devices connected in one direction. The continuous form is cut across its length in the second cutting part 80. The second cutting part 80 includes a rotary die cutter 82 having a cutting blade 81 around its circumference and an anvil roller 83, between which the continuous form passes and is cut into individual heat generating devices 100. When the cutting line of the heat generating element 10A in the first cutting part 40 is a straight line, it is preferred that the cutting line in the second cutting part 80 be also a straight line. When the cutting line of the heat generating element 10A in the first cutting part 40 is a curved line, it is preferred that the cutting line in the second cutting part 80 be also curved along the curved cutting line. As shown in FIG. 3, the resulting heat generating device 100 has the heat generating element 10 completely enclosed by the first cover sheet 4 and the second cover sheet 5. The heat generating device 100 has the first cover sheet 4 on the side of the heat generating element 10 having the heat generating layer formed and the second cover sheet 5 on the other side having no heat generating layer formed.

Figure 4:
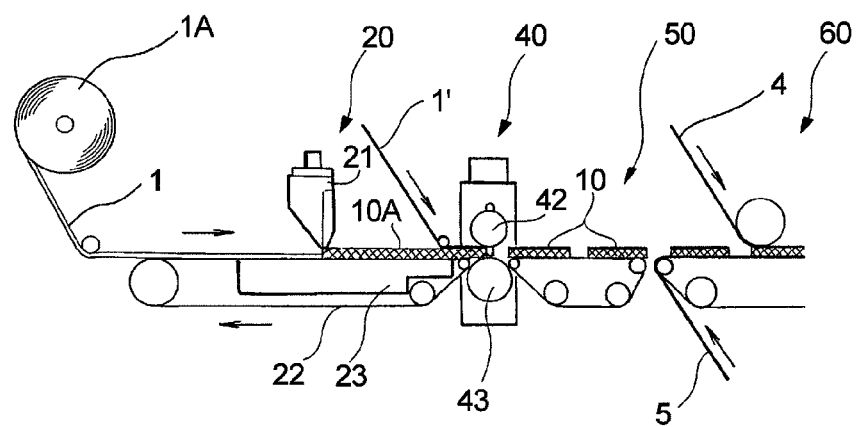
FIG. 4 is a schematic illustration of another example of an apparatus suitably used to produce the heat generating element or device of the invention.

Another example of an apparatus that is suitably used for the production of the heat generating device of the invention is shown in FIG. 4. The difference of the apparatus of FIG. 4 from that shown in FIG. 2 is that the apparatus of FIG. 4 operates to feed and superpose a continuous-length base sheet 1' onto the heat generating layer at a position between the coating part 20 and the first cutting part 40. By using this apparatus, a heat generating element having a heat generating layer sandwiched in between two base sheets 1 and 1', which may be the same or different, is obtained easily. Either one of the base sheet 1 on which the coating material is applied and the base sheet 1' which is to be disposed on the heat generating layer may not contain superabsorbent polymer particles, but it is preferred for both of them to contain superabsorbent polymer particles.

While in the method 1 the coating material applied to the base sheet is a heat generative composition, application of the heat generative composition may be replaced with application of a coating material containing oxidizable metal particles but not containing an electrolyte, followed by adding an aqueous electrolyte solution to the coated side of the base sheet. This method will be called method 2. Specifically, a coating material containing oxidizable metal particles, a reaction accelerator, water, a thickener, and a surfactant is prepared, and the coating material is applied to a base sheet to form a coating layer, and an aqueous electrolyte solution containing an electrolyte and water is added to the coating layer. The concentration of each component of the coating material and the aqueous electrolyte solution and the amounts to be used of the coating material and the aqueous electrolyte solution are adjusted so that the contents of the components in the resulting heat generating element may fall within the respective ranges recited earlier.

The method 2 allows for applying coating materials different in build-up or water content in an alternative stripe pattern or adding aqueous electrolyte solutions different in concentration or amount of addition in an alternate stripe pattern, thereby to form a high water content portion and a low water content portion in an alternate stripe pattern extending in one planar direction of the heat generating element.

A preferred embodiment of the method 2 includes (2-1) a coating step and (2-2) an electrolyte addition step as hereinafter described. A preferred embodiment of the method for the production of a heat generating device according to the present embodiment includes, after the steps for the production of the heat generating element, (2-3) a covering and sealing step in which the resulting heat generating element is enclosed in an enclosing material to make a heat generating device (the step of enclosing in the production of a heat generating device).

(2-1) Coating Step

In the coating step, one of the steps for the production of a heat generating element, a coating material containing oxidizable metal particles but not containing an electrolyte is applied to the base sheet. As used herein, the term "electrolyte" is intended to mean an electrolyte that is added for the purpose of dissolving an oxide formed on the oxidizable metal particles. Accordingly, the phrase "not containing an electrolyte" does not mean that the coating material does not contain any electrolyte but that the coating material does not substantially contain an electrolyte that is to be added in the subsequent electrolyte addition step. That is, when in using tap water as a water source, a chlorine-containing component present in tap water is not included under the term "electrolyte". In other words, a substance incapable of assuring a sustained given level of heat generation by the heat generating element is not included under the term "electrolyte". Since the coating material is substantially free from an electrolyte, oxidation of the oxidizable metal particles does not proceed before the electrolyte addition step. Accordingly, there is no particular need to take a measure to block oxidizable metal particles from air. Furthermore, an oxidation reaction in a coating material is inhibited from proceeding during storage of the coating material, which leads to reduction of heat generation loss. Moreover, in the absence of an electrolyte, the components in the coating material maintain good dispersibility before and during application. For instance, even when the coating material is left to stand before application, the coating material is less likely to suffer from agglomeration of the oxidizable metal particles, which might lead to settlement of the agglomerates or separation of water. According to the method 2 for the production of the heat generating element, because the coating material does not positively contain an electrolyte, the coating material adhering to the paddle of a kneading machine, the inner wall of a tank, and so on hardly undergoes oxidation during the preparation of the coating material in preparation equipment, such as a tank, and during application of the coating material. This permits minimizing the use of a highly anticorrosive expensive material to make the manufacturing equipment.

The coating material usually contains a reaction accelerator and water in addition to the oxidizable metal particles. The coating material may further contain a thickener and a surfactant to improve the dispersibility of the solid matter. The coating material containing the components described is continuously applied to a side of a base sheet, for example, a continuous-length base sheet. To carry out the application, any known coating techniques, like the coating method adopted in the method 1, may be used with no restriction.

The coating material for the formation of a heat generating layer preferably contains 1 to 20 parts, more preferably 2 to 14 parts, of a reaction accelerator; 25 to 85 parts, more preferably 35 to 75 parts, of water; 0.05 to 10 parts, more preferably 0.1 to 5 parts, of a thickener; and 0.1 to 15 parts, more preferably 0.2 to 10 parts, of a surfactant each per 100 parts of oxidizable metal particles. Water is preferably present in an amount of 18% to 48%, more preferably 23 to 43%, by mass taking the total mass of the coating material as 100%. The viscosity of the coating material at 23° C. and 50% RH is preferably 500 to 30,000 Pa·s, more preferably 1,000 to 15,000 mPa·s. The viscosity was measured with a Brookfield viscometer equipped with a No. 4 rotor at a rotor speed of 6 rpm.

As a result of applying the coating material, a coating layer continuous over a side of the base sheet is formed. Since the base sheet contains superabsorbent polymer particles, water in the coating material is absorbed and retained by the superabsorbent polymer to a moderate degree so that the water content of the coating layer becomes lower than that of the coating material. As a result, the coating layer reduces in flowability. The fact that the base sheet contains hydrophilic fibers also ensures that the water of the coating material is moderately absorbed and retained by the base sheet to reduce the water content of the coating layer. The coating layer is a portion that becomes a heat generating layer upon receipt of an aqueous electrolyte solution supplied thereto. Accordingly, the water content of the coating layer is a value measured for the portion of the coating layer above the surface of the base sheet similarly to the water content of the heat generating layer. The portion of the coating layer embedded in the base sheet is excluded from the object of water content measurement. The water content of the coating layer is measured in the same manner as for the water content of the heat generating layer.

The application of the coating material is preferably carried out so that the water content of the resulting coated sheet composed of the base sheet and the coating layer may fall within the range of 50% to 95%, more preferably 60% to 90%, of the water content of a finally obtained heat generating element, taking into consideration the coating properties of the coating material and in order for the heat generating element obtained by the subsequent addition of an aqueous electrolyte solution to perform desired heat generating performance. The water content of the sheet composed of the base sheet and the coating layer is obtained by measuring the mass of the sheet in a nitrogen environment, drying the sheet in an drying oven at 105° C. in vacuo for 2 hours to be freed of water, measuring the mass of the dried sheet, and calculating the difference in mass before and after the drying. The coating weight of the coating material is preferably 150 to 4,600 g/m², more preferably 300 to 2,200 g/m².

The coating step is preferably carried out while sucking the base sheet from the opposite side to the side being coated (the opposite side will hereinafter be sometimes called a non-coated side) so as to draw part of the coating material and the solid matter of the coating material including the oxidizable metal particles into the fiber-to-fiber spaces of the base sheet. Having the oxidizable metal particles and the like drawn into the base sheet improves the integrity between the coating layer or heat generating layer and the base sheet, thereby effectively preventing fall-off of the heat generating layer from the base sheet before, during, and after use. The suction from the non-coated side may be conducted, instead of simultaneously with the application of the coating material, after applying the coating material and before adding an aqueous electrolyte solution. The suction force is preferably 100 to 10,000 Pa, more preferably 500 to 5,000 Pa. The suction force is measured with a Manostar gauge (differential low pressure gauge) attached inside the box of the suction conveyor.

(2-2) Electrolyte Addition Step

In the electrolyte addition step, one of the steps for the production of a heat generating element, an aqueous electrolyte solution is added to the coated side of the base sheet. Addition of an aqueous electrolyte solution may be performed by dropwise addition or spraying through a nozzle, application with a brush, die coating, and the like. To prevent the aqueous electrolyte solution from splashing to the surroundings, clogging the spout, and contaminating the production equipment, the aqueous electrolyte solution is preferably supplied by dropwise addition or spraying from a nozzle.

On electrolyte addition, the coating layer having been formed on one side of the base sheet acquires the aqueous electrolyte solution to become the above-described heat generating layer. In this stage, the water content of the coating layer is lower than that of the coating material since it has been absorbed and retained by the superabsorbent polymer included in the base sheet. Therefore, the heat generating layer formed by the addition of the aqueous electrolyte solution does not have so much increased flowability and will not impede air permeability of an air permeable sheet disposed thereon in the subsequent step. In particular, when the base sheet is sucked from its non-coated side during the application and/or after the application and before the aqueous electrolyte solution addition as earlier noted, freedom in selecting the concentration or the amount of the aqueous electrolyte solution will increase.

If the base sheet is strongly sucked from its non-coated side during the addition of the aqueous electrolyte solution, it is likely that the water content necessary for heat generation is not held in the heat generating layer. It is therefore desirable that suction not at all be conducted during the aqueous electrolyte solution addition or be performed during the aqueous electrolyte solution addition under a milder condition than the condition of the suction during the coating step or after the coating step and before the addition of the aqueous electrolyte solution. Where needed, nevertheless, the condition of suction during the aqueous electrolyte solution addition may be stronger than that adopted during the coating step or after the coating step and before the aqueous electrolyte solution addition.

Seeing that the electrolyte added to the base sheet is diluted with the water content remaining in the base sheet, it is preferred that the aqueous electrolyte solution to be added in the electrolyte addition step contain the electrolyte in a higher ratio (usually equivalent to concentration) than the ratio of the electrolyte to the sum of the electrolyte and water in the heat generating element to assure that the resulting heat generating element is capable of satisfactory heat generating performance. The aqueous electrolyte solution to be added preferably contains the electrolyte in a ratio of 3% to 35%, more preferably 5% to 30%, by mass and is preferably applied (spread) in an amount of 30 to 400 g/m², more preferably 50 to 300 g/m². The amount of the electrolyte to be added (on a solid basis) is preferably 0.5 to 15 parts, more preferably 1 to 10 parts, per 100 parts of the oxidizable metal particles added in the preceding coating step and present in the same region.

(2-3) Step of Covering and Sealing Heat Generating Device (Enclosing Step)

After a continuous-length heat generating element is obtained by the above described operation, the heat generating element is covered in the covering and sealing step following the steps for the production of a heat generating element. Prior to the covering operation, it is preferred that the continuous-length heat generating element be cut across its length into individual heat generating elements. The individual heat generating elements are transported in one direction with a prescribed spacing between them. A continuous-length first cover sheet is overlaid on the heat generating layer side of the running heat generating elements, and a continuous-length second cover sheet is applied to the other side of the heat generating elements. The extended portion of the first cover sheet and the extended portion of the second cover sheet, which extend outward from the individual heat generating elements, are bonded together by a prescribed means. The bonding is performed outside the opposite lengthwise edges and the opposite transverse edges of the heat generating element by, for example, fusion bonding, ultrasonic bonding, or adhesion with an adhesive.

Because the heat generating layer decreases in water content to have reduced flowability by the time when the first cover sheet is overlaid on the heat generating layer, the problem of the heat generating layer sticking to the first cover sheet is avoided. As a result, the air permeability of the first cover sheet is successfully maintained.

A continuous form having a plurality of heat generating devices unidirectionally connected in series is thus obtained. The continuous form is cut across the length between adjacent heat generating devices to yield desired heat generating devices. The resulting heat generating device is sealed in an oxygen-barrier package in the subsequent step.

In carrying out the method 2, it is preferred to use any means for maintaining the production line in a non-oxidative atmosphere so as to inhibit oxidation of the oxidizable metal during the production steps, particularly after the electrolyte addition step.

While in the above description the continuous-length heat generating element is cut across the length before the covering and sealing step (2-3), the continuous-length heat generating element may be cut prior to the electrolyte addition step (2-2), and the individual coated and cut base sheets may be supplied with the electrolyte in the electrolyte addition step (2-2).

Figure 5:
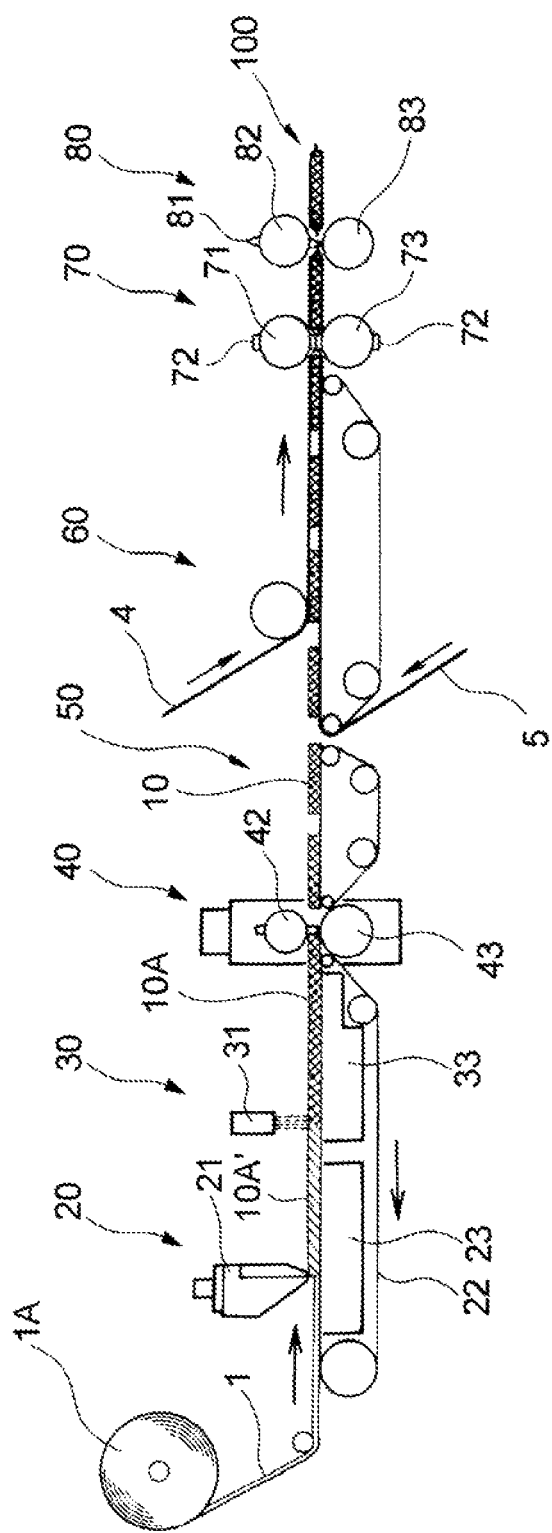
FIG. 5 is a schematic illustration of still another example of an apparatus suitably used to produce the heat generating element or device of the invention.

FIG. 5 illustrates an example of an apparatus preferably used to carry out the method 2. The apparatus includes a coating part 20 where a coating material is applied, an electrolyte addition part 30, a first cutting part 40, a re-pitching part 50, a covering part 60, a sealing part 70, and a second cutting part 80.

The coating part 20 is identical to the coating part 20 of the apparatus shown in FIG. 2. A continuous-length base sheet 1 unrolled from a stock roll 1A of the base sheet is transported by the endless belt 22, and a coating material is applied to one side of the base sheet 1 with the die coater 21 to form a coating layer on that side. While the base sheet 1 is transported by the endless belt 22, the suction box 23 operates to stabilize the transportation and suck water in the coating material to control the amount of water to be absorbed and retained by the base sheet 1. After the coating material is applied, the water of the coating material is absorbed by the base sheet 1 so that the water content of the coating layer is lower than that of the coating material. It follows that the coating layer reduces in flowability.

The electrolyte addition part 30 has a nozzle 31 through which an aqueous electrolyte solution is added dropwise, an endless belt 22 formed of wire mesh that faces the orifices of the nozzle 31 and runs in the direction indicated by the arrow, and a suction box 33 that faces the orifices of the nozzle 31 across the endless belt 22. The coated base sheet is transported by the endless belt 22 from the coating part 20 to the electrolyte addition part 30, where an aqueous electrolyte solution is dropwise fed from the orifices of the nozzle 31 to the coated side of the base sheet to form a heat generating layer. While the base sheet 1 is being transported in the electrolyte addition part 30, the suction box 33 may operate to stabilize the transportation. On adding the aqueous electrolyte solution after the coating, an electrolyte concentration suitable to heat generation is secured in the heat generating layer and, at the same time, the aqueous electrolyte solution added is absorbed and retained by the base sheet while being diluted with water present in the coating layer and the base sheet 1. It follows that the heat generating layer (coating layer) comes to have a suitable water content and a suitable electrolyte concentration. The suction by the suction box during spreading the aqueous electrolyte solution ensures penetration of the aqueous electrolyte solution inside the base sheet.

The thus formed continuous-length heat generating element 10A is cut in the transverse direction in the first cutting part 40. The operation of the first cutting part 40 is equivalent to that of the first cutting part 40 of the apparatus shown in FIG. 2.

The running pitch of the individual heat generating elements 10 is changed in the re-pitching part 50 so that they may be transported at a given spacing therebetween. The details of the re-pitching operation are the same as those in the re-pitching part 50 of the apparatus shown in FIG. 2.

The re-pitched heat generating elements 10 are forwarded to the covering part 60, where the individual heat generating elements 10 are entirely covered with a continuous-length first cover sheet 4 and a continuous-length second cover sheet 5. The details of the covering operation are the same as those of the covering part 60 of the apparatus shown in FIG. 2.

There is obtained a continuous form of a plurality of heat generating devices connected in one direction. The continuous form is cut across its length in the second cutting part 80. The details of the cutting are the same as those of the second cutting part 80 of the apparatus shown in FIG. 2.

Figure 6:
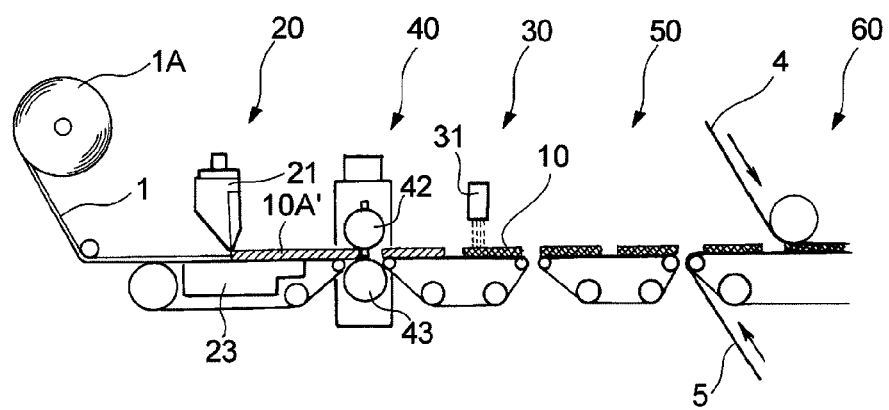
FIG. 6 is a schematic illustration of still another example of an apparatus suitably used to produce the heat generating element or device of the invention.

FIG. 6 illustrates another example of the apparatus preferably used to carry out the method 2. The apparatus of FIG. 6 has the same structure as the apparatus of FIG. 5, except that the re-pitching part 50 is differently positioned and that the electrolyte addition part 30 does not have a suction box. The apparatus of FIG. 5 has the first cutting part 40 between the electrolyte addition part 30 and the re-pitching part 50, whereas the apparatus of FIG. 6 has the first cutting part 40 between the coating part 20 and the electrolyte addition part 30. The electrolyte addition part 30 of the apparatus of FIG. 6 does not have a sucking means, like a suction box, that sucks the base sheet from the non-coated side. The apparatus of FIG. 6 has otherwise the same structure as the apparatus of FIG. 5.

While in the method 2 application of a coating material containing oxidizable metal particles and not containing an electrolyte is followed by addition of an aqueous electrolyte solution, it is possible that the addition of an aqueous electrolyte solution precedes the application of a coating material containing oxidizable metal particles and not containing an electrolyte. This method will hereinafter be referred to as a method 3. When the method 3 is adopted, too, the addition of the aqueous electrolyte solution and/or the application of the coating material may be carried out in a stripe pattern to form a high water content portion and a low water content portion in an alternate stripe pattern extending in a planar direction of the heat generating element.

A preferred embodiment of the method 3 includes (3-1) an electrolyte addition step and (3-2) a coating step as described below. A still preferred embodiment of the method 3 further includes (3-3) a covering and sealing step in which the resulting heat generating element is enclosed in an enclosing material to provide a heat generating device.

(3-1) Electrolyte Addition Step

In the electrolyte addition step, one of the steps for the production of a heat generating element, an aqueous electrolyte solution containing an electrolyte is added to one side of a base sheet. For example, an aqueous electrolyte solution is continuously applied to one side of a continuous-length base sheet. Addition of the aqueous electrolyte solution may be performed by dropwise addition or spraying through a nozzle, application with a brush, die coating, and the like. To prevent the aqueous electrolyte solution from splashing to the surroundings and clogging the spout, the aqueous electrolyte solution is preferably supplied by dropwise addition or spraying from a nozzle.

The aqueous electrolyte solution to be added preferably contains the electrolyte in a concentration of 3% to 35%, more preferably 5% to 30%, by mass. The amount of the electrolyte to be added (on a solid basis) is preferably 0.5 to 15 parts, more preferably 1 to 10 parts, per 100 parts of the oxidizable metal particles added in the coating step described later and present in the same region. The amount of the aqueous electrolyte solution to be added (spread) is preferably 30 to 400 $g/m^2$, more preferably 50 to 300 $g/m^2$.

It is preferred that the aqueous electrolyte solution to be added in the electrolyte addition step contain the electrolyte in a higher ratio than the ratio of the electrolyte in the heat generating element to the sum of the electrolyte and water in the heat generating element. Furthermore, in the electrolyte addition step, the aqueous electrolyte solution is preferably added in an amount larger than the value obtained by multiplying the saturation capacity of the superabsorbent polymer for the aqueous electrolyte solution by the mass of the superabsorbent polymer present in the base sheet, the saturation capacity for the aqueous electrolyte solution being measured by making use of JIS K7224. JIS K7224 specifies a testing method for water absorption rate of superabsorbent resins, which is a method for determining an absorption rate by the vortex method known to represent a liquid fixing ability of an absorbent resin when the absorbent resin is forcedly exposed to the liquid. The term "superabsorbent resin" and the term "absorbent polymer" are equivalent. As used therein, the phrase "making use of JIS K7224" means to follow the standards specified in JIS K7224 with respect to the preparation of a sample, a test liquid, testing tools, and the like and the testing procedures. The absorption capacity of a superabsorbent polymer is determined according to the following procedures, including the conditions not specified in JIS K7224, such as for the measurement of amount of absorption.

Measurement of Saturation Capacity of Superabsorbent Polymer Making Use of JIS K7224

Fifty grams of an aqueous electrolyte solution having the same concentration as the aqueous electrolyte solution added in the electrolyte addition step and a magnetic stir bar (diameter at the middle: 8 mm; diameter at both ends: 7 mm; length: 30 mm; coated with a fluororesin) are put in a 100 ml glass beaker and stirred on a magnetic stirrer (HPS-100 from AS ONE Corp.) at 600±60 rpm to create a vortex. Two grams of a superabsorbent polymer used in the base sheet is poured into the center of the vortex. The operation described so far is in accordance with JIS K7224 (1996). Ten minutes after the addition of the superabsorbent polymer, the amount absorbed by the superabsorbent polymer is measured as follows, from which the absorption amount per part by mass of the superabsorbent polymer is calculated. The superabsorbent polymer having absorbed the aqueous electrolyte solution for 10 minutes is put in a polyester mesh bag (mesh size: 255/25.4 mm) measuring 100 mm by 100 mm, whose mass has been measured beforehand. The bag with the contents is dewatered in a centrifugal dewaterer at 2,000 rpm for 10 minutes, followed by weighing. The mass of the superabsorbent polymer before absorption (=2 g) and the mass of the bag are subtracted from the measured mass to give the absorption amount by the superabsorbent polymer. The thus obtained value is taken as the saturation absorption of the superabsorbent polymer for the aqueous electrolyte solution at the concentration used in the electrolyte addition step. The measurement is taken in quintuplicate (n=5). The highest and the lowest value are discarded, and the average of the remainder is taken as a measured value. The measurements are carried out in an environment of 23±2° C. and 50±5% RH. The samples are conditioned in the same environment for at least 24 hours before the measurement.

(3-2) Coating Step

In the coating step as one of the steps for the production of a heat generating element, a coating material containing oxidizable metal particles but not containing an electrolyte is applied to the base sheet after the electrolyte addition step (3-1) on the side having received the aqueous electrolyte solution. The coating step may be performed by, for example, continuously applying the coating material to the side to which the aqueous electrolyte solution has continuously been added. As used herein, the term "electrolyte" is intended to mean an electrolyte that is added for the purpose of dissolving an oxide formed on the oxidizable metal particles. Accordingly, the phrase "not containing an electrolyte" does not mean that the coating material does not contain any electrolyte but that the coating material does not substantially contain the electrolyte added in the preceding electrolyte addition step. That is, when in using tap water as a water source, a chlorine-containing component present in tap water is not included under the term "electrolyte".

The coating material usually contains a reaction accelerator and water in addition to the oxidizable metal particles. The coating material may further contain a thickener and a surfactant to improve the dispersibility of the solid contents. The coating material containing the components described is continuously applied to one side of a base sheet, for example, a continuous-length base sheet. Any known coating method may be used, such as roller coating, die coating, screen printing, gravure coating, knife coating, or contour coating. Die coating is preferred in view of ease of coating, ease of controlling the coating build-up, and uniform application of the coating material.

The coating material for the formation of a heat generating layer preferably contains 1 to 20 parts, more preferably 2 to 14 parts, of a reaction accelerator; 25 to 85 parts, more preferably 35 to 75 parts, of water; 0.05 to 10 parts, more preferably 0.1 to 5 parts, of a thickener; and 0.1 to 15 parts, more preferably 0.2 to 10 parts, of a surfactant each per 100 parts of oxidizable metal particles. Water is preferably present in an amount of 18% to 48%, more preferably 23 to 43%, by mass taking the total mass of the coating material as 100%.

The coating weight of the coating material is preferably 150 to 4,600 g/m$^2$, more preferably 300 to 2,200 g/m$^2$. The viscosity of the coating material at 23° C. and 50% RH is preferably 500 to 30,000 Pa·s, more preferably 1,000 to 15,000 mPa·s. The viscosity was measured with a Brookfield viscometer equipped with a No. 4 rotor.

The method 3 including the electrolyte addition step (3-1) and the coating step (3-2) allows for continuous production of a heat generating element having a base sheet formed of a fibrous sheet containing superabsorbent polymer particles and a fibrous material and a layer of a heat generative composition (heat generating layer) containing oxidizable metal particles, an electrolyte, and water provided on the base sheet. Since the coating material is substantially free from an electrolyte, oxidation of the oxidizable metal particles does not proceed. Accordingly, there is no particular need to take a measure to block oxidizable metal particles from air in the coating step. Furthermore, the oxidation reaction in the coating material is inhibited from proceeding during storage of the coating material, which leads to reduction of heat generation loss. Moreover, in the absence of an electrolyte, the components in the coating material maintain good dispersibility before and during application. For example, even when the coating material is left to stand before application, the coating material is less likely to suffer from agglomeration of the oxidizable metal particles, which might lead to settlement of the agglomerates or separation of water. According to the method 3, because the coating material does not positively contain an electrolyte as noted, the coating material adhering to the paddle of a kneading machine, the inner wall of a tank, and so on hardly undergoes oxidation during the preparation of the coating material in preparation equipment, such as a tank, and during application of the coating material. This permits minimizing the use of a highly anticorrosive expensive material to make the manufacturing equipment.

According to the method 3, when the coating material containing oxidizable metal particles is applied, there already exists an aqueous electrolyte solution in the base sheet that has been added in the precedent step. As a result, the aqueous electrolyte solution is made to uniformly contact with the oxidizable metal particles to provide a heat generating element having a reduced loss of heat generation.

When, in particular, the aqueous electrolyte solution to be added to the base sheet containing superabsorbent polymer particles in the electrolyte addition step has a higher electrolyte concentration than the ratio of the electrolyte in the heat generating element to be produced to the sum of the electrolyte and water in the heat generating element, the aqueous electrolyte solution added is less absorbable by the superabsorbent polymer and therefore uniformly distributed throughout the base sheet more easily. When, in particular, the aqueous electrolyte solution is added to the base sheet containing superabsorbent polymer particles in an amount larger than the value obtained by multiplying the saturation capacity of the superabsorbent polymer measured by making use of JIS K7224 by the mass of the superabsorbent polymer present in the base sheet, the part of the aqueous electrolyte solution that is not absorbed by the superabsorbent polymer is uniformly distributed throughout the base sheet even more easily. Applying the coating material to the base sheet in that state causes the oxidizable metal particles to come into uniform contact with the aqueous electrolyte solution throughout the base sheet, thereby providing a heat generating element having a further reduced loss of heat generation. Even when such a high concentration aqueous electrolyte solution is added, the water-containing coating material applied thereafter is mixed with the aqueous electrolyte solution thereby to reduce the concentration of the aqueous electrolyte solution. As a result, the superabsorbent polymer has enhanced absorbency, and the finally obtained heat generating element has a water concentration suited to cause the oxidizable metal particles to generate heat.

In order to uniformly distribute the aqueous electrolyte solution throughout the base sheet to secure a prescribed heat generation temperature during use, it is preferred that the aqueous electrolyte solution is added in the electrolyte addition step in such a manner that the amount of the aqueous electrolyte solution is 10% to 80%, more preferably 20% to 50%, relative to the sum of the electrolyte and water contained in the heat generating element. It is also preferred that the aqueous electrolyte solution be added in the electrolyte addition step in an amount 1 to 10 times, more preferably 1.5 to 6 times, the value obtained by multiplying the saturation absorption of the superabsorbent polymer by the mass of the superabsorbent polymer present in the base sheet.

Compared with a method of making a heat generating element by using a base sheet containing no superabsorbent polymer particles, the method 3 avoids the need for a dewatering step or a heat-drying step due to using a base sheet containing superabsorbent polymer particles. Thus, the method 3 achieves reduction of the number of steps involved or the scale of the production equipment, and oxidation of the heat generative substance during the production steps is minimized.

When in the method 3 the base sheet having been coated with an aqueous electrolyte solution on one side thereof is sucked from the other side (opposite to the side being coated, hereinafter sometimes called a non-coated side) so as to draw the oxidizable metal particles into the fiber-to-fiber spaces of the base sheet, the base sheet has improved integrity with the coating layer or the heat generating layer. As a result, fall-off of the heat generating layer from the base sheet is effectively prevented before, during, and after use. The suction force is preferably 100 to 10,000 Pa, more preferably 500 to 5,000 Pa. The suction force is measured with a Manostar gauge attached inside the box of the suction conveyor.

(3-3) Covering Step

After a continuous-length heat generating element is obtained by the above described operation, the heat generating element is enclosed in an enclosing material in the covering and sealing step subsequent to the steps for the production of the heat generating element. The details of this step are the same as those discussed for the covering step (2-3).

Because the heat generating layer decreases in water content to have reduced flowability as a result of absorption by the superabsorbent polymer by the time when the first cover sheet is overlaid on the heat generating layer, the problem of the heat generating layer sticking to the first cover sheet is avoided. As a result, the air permeability of the first cover sheet is successfully maintained.

A continuous form having a plurality of heat generating devices unidirectionally connected in series is thus obtained. The continuous form is then cut across the length between adjacent heat generating devices to yield desired heat generating devices. The resulting heat generating device is sealed in an oxygen-barrier package in the subsequent step.

In carrying out the method 3, any means for maintaining the production line in a non-oxidative atmosphere may be used if desired so as to inhibit oxidation of the oxidizable metal during the production steps.

Figure 7:
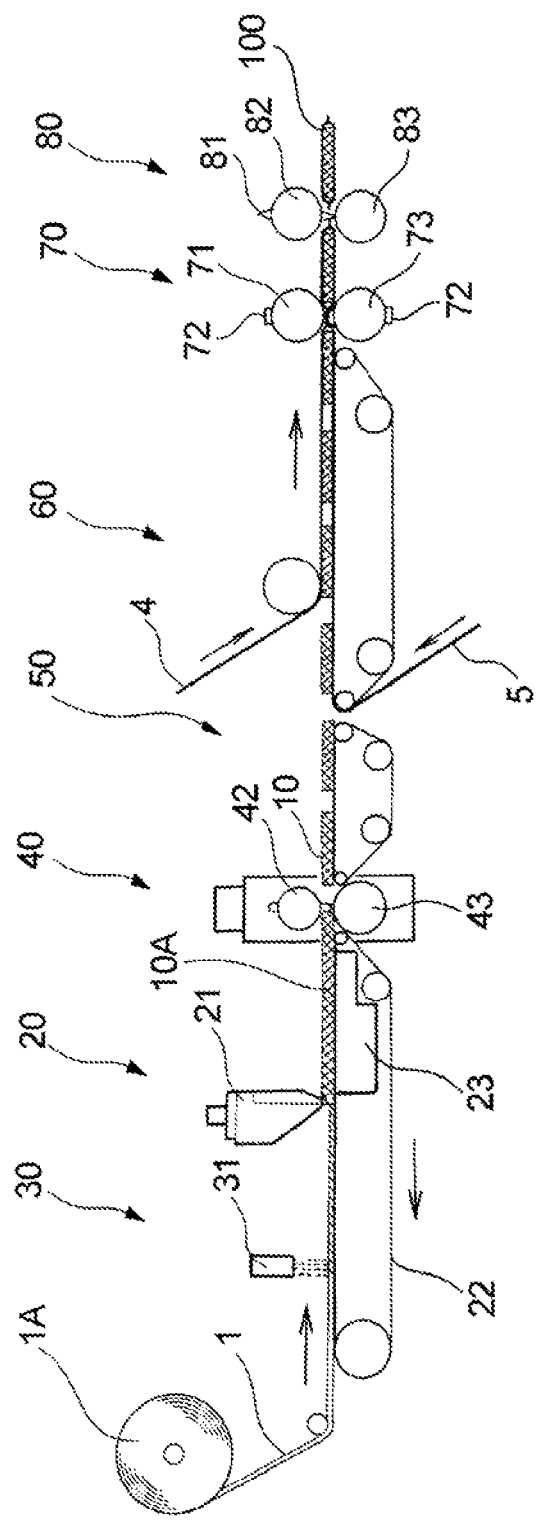
FIG. 7 is a schematic illustration of still another example of an apparatus suitably used to produce the heat generating element or device of the invention.

FIG. 7 illustrates an example of an apparatus preferably used to carry out the method 3. The apparatus includes an electrolyte addition part 30, a coating part 20, a first cutting part 40, a re-pitching part 50, a covering part 60, a sealing part 70, and a second cutting part 80.

The electrolyte addition part 30 has a spray nozzle 31 through which an aqueous electrolyte solution is sprayed and an endless belt 22 formed of wire mesh that faces the orifices of the spray nozzle 31 and runs in the direction indicated by the arrow. A continuous-length base sheet 1 unrolled from a stock roll 1A is transported by the endless belt 22 from the electrolyte addition part 30 to the coating part 20. An aqueous electrolyte solution is sprayed from the orifices of the spray nozzle 31 to one side of the base sheet 1 at the electrolyte addition part 30. Fed by spraying, the aqueous electrolyte solution is uniformly distributed throughout (both in the planar and the thickness direction) the base sheet 1. The spray nozzle 31 may be a nozzle through which the aqueous electrolyte solution is dropwise fed.

The coating part 20 is identical to the coating part 20 of the apparatus shown in FIG. 2. After addition of the aqueous electrolyte solution, the continuous-length base sheet 1 is transported by the endless belt 22 from the electrolyte addition part 30 to the coating part 20, where a coating material 2 containing oxidizable metal particles 2a according to the aforementioned formulation is applied to the electrolyte-added side of the base sheet 1 with the die coater 21 to form a heat generating layer. While the base sheet 1 is transported through the coating part 20, a suction box 23 may operate to stabilize the transportation and suck the applied coating material 2. The applied coating material mixes with the aqueous electrolyte solution previously incorporated into the base sheet, and the water of the coating material is absorbed by the base sheet so that the electrolyte concentration is adjusted to secure an electrolyte concentration suitable for heat generation in the heat generating layer. By applying the coating material after the addition of the aqueous electrolyte solution, the heat generative composition and the electrolyte are easily uniformly brought into contact with each other to provide a heat generating element having a reduced loss of heat generation.

The thus formed continuous-length heat generating element 10A is cut in the transverse direction in the first cutting part 40. The operation of the first cutting part 40 is identical to that of the first cutting part 40 of the apparatus shown in FIG. 2.

The running pitch of the individual heat generating elements 10 is changed in the re-pitching part 50 so that they may be transported at a given spacing therebetween. The details of the re-pitching operation are the same as those of the re-pitching part 50 of the apparatus shown in FIG. 2.

The re-pitched heat generating elements 10 are forwarded to the covering part 60, where the individual heat generating elements 10 are entirely covered with a continuous-length first cover sheet 4 and a continuous-length second cover sheet 5. The details of the covering operation are the same as those of the covering part 60 of the apparatus shown in FIG. 2.

There is thus obtained a continuous form of a plurality of heat generating devices connected in series in one direction. The continuous form is cut across its length in the second cutting part 80. The details of the cutting are the same as those of the second cutting part 80 of the apparatus shown in FIG. 2.

The method 2 that is carried out using the apparatus shown in FIG. 5 or 6 and the method 3 that is carried out using the apparatus shown in FIG. 7 may include the step of overlaying a second base sheet 1', which may be the same or different from the base sheet 1, on the heat generating layer formed on the base sheet 1 similarly to the method using the apparatus shown in FIG. 4.

As still another method for making a heat generating element, a method 4 described below may be employed. The method 4 preferably includes (4-1) the step of applying a coating material (coating step) and (4-2) the step of adding an electrolyte. The step (4-1) may precede the step (4-2), or the step (4-2) may precede the step (4-1). Otherwise, the steps (4-1) and (4-2) may be carried out simultaneously. In any case, a step of covering and sealing may follow the making of a heat generating element, in which the heat generating element is enclosed in an enclosing material partly having air permeability to provide a heat generating device.

(4-1) Coating Step

In the coating step, one of the steps of the method 4, a coating material containing at least oxidizable metal particles and water but not containing an electrolyte to a base sheet. As used herein, the term "electrolyte" is intended to mean an electrolyte that is added for the purpose of dissolving an oxide formed on the oxidizable metal particles. Accordingly, the phrase "not containing an electrolyte" does not mean that the coating material does not contain any electrolyte but that the coating material does not substantially contain an electrolyte that is to be added in the subsequent electrolyte addition step. When in using tap water as a water source, a chlorine-containing component present in tap water is not included under the term "electrolyte".

The coating material is prepared by, for example, mixing an oxidizable metal and a reaction accelerator, adding water to the mixture, followed by mixing to uniformity. Even when the surface of the oxidizable metal is damaged by, for example, a reaction accelerator described later to be oxidized temporarily, the oxidized film does not dissolve because of the absence of an electrolyte so that further progress of oxidation is inhibited. Oxidation of the oxidizable metal does not substantially proceed until the oxidizable metal comes into contact with an electrolyte. Therefore, progress of oxidation during the storage of the coating material is inhibited, leading to reduction in loss of heat generation. Moreover, in the absence of an electrolyte, the components in the coating material maintain good dispersibility before and during application. For example, even when the coating material is left to stand before application, the coating material is less likely to suffer from agglomeration of the oxidizable metal particles, which could lead to settlement of the agglomerates or separation of water. In the case when the step of coating is followed by the electrolyte addition step, there is no particular need to take a measure to block oxidizable metal particles from air in the coating step.

According to the method 4, since the coating material does not positively contain an electrolyte, the paddle of a kneading machine, the inner wall of a tank, and so on hardly undergoes corrosion attributed to an electrolyte during the preparation of the coating material in preparation equipment, such as a tank, and during application of the coating material prepared. This permits minimizing the use of a highly anticorrosive expensive material to make the manufacturing equipment.

The coating material may contain a thickener or a surfactant to improve dispersibility of the solid matter. Useful as a thickener are, for example, substances capable of absorbing water or a metal chloride aqueous solution to increase the consistency or impart thixotropy to the coating material. Examples of such substances include bentonite, stearic acid salts, polyacrylic acid salts (e.g., sodium polyacrylate), gelatin, tragacanth gum, locust bean gum, guar gum, gum arabic, alginic acid salts (e.g., sodium alginate), pectin, carboxyvinyl polymers, starch-based water absorbents (e.g., dextrin, α-starch, and starch for processing), polysaccharide thickeners (e.g., carrageenan and agar), and cellulose-based thickeners (e.g., carboxymethyl cellulose, ethyl acetate cellulose, hydroxyethyl cellulose, methyl cellulose, and hydroxypropyl cellulose). Examples of useful surfactants include anionic surfactants containing as a main component an aromatic sulfonic acid-formalin condensate or a special carboxylic acid type polymeric surfactant.

The coating material preferably contains 25 to 85 parts, more preferably 35 to 75 parts, of water per 100 parts of oxidizable metal particles. If necessary, the coating material preferably contain 1 to 20 parts, more preferably 2 to 14 parts of a reaction accelerator; 0.05 to 10 parts, more preferably 0.1 to 5 parts, of a thickener; and 0.1 to 15 parts, more preferably 0.2 to 10 parts, of a surfactant each per 100 parts of the oxidizable metal particles.

It is preferred for the coating material to have such a water content that, when the coating layer formed by application of the coating material and the electrolyte hereinafter described are brought into contact with each other, the electrolyte dissolves and diffuse into the coating layer to form a desired heat generating layer. From this viewpoint, the water content is preferably 18% to 48%, more preferably 23% to 43%, by mass based on the total mass of the coating material.

The viscosity of the coating material having the above described composition is preferably 500 to 30,000 Pa·s, more preferably 1,000 to 15,000 mPa·s, even more preferably 1,000 to 10,000 mPa·s, at 23° C. and 50% RH. The viscosity was measured with a Brookfield viscometer equipped with a No. 4 rotor at a rotor speed of 6 rpm.

In the case when the base sheet is air permeable, it is preferred that the base sheet is sucked from the side opposite to the side being coated (hereinafter also referred to as a non-coated side) during applying the coating material so that the solid matter of the coating material, primarily oxidizable metal particles, may be drawn into the microvoids of the base sheet. Depending on the kind of the base sheet or the composition of the coating material, the base sheet is able to take up the solid matter of the coating material into its microvoids without the aid of suction. Having the oxidizable metal particles and the like drawn into the base sheet improves the integrity between the heat generating layer and the base sheet, thereby effectively preventing fall-off of the heat generating layer from the base sheet before, during, and after use. The suction from the non-coated side may be carried out, instead of simultaneously with the application of the coating material, after applying the coating material. The suction force is preferably 100 to 10,000 Pa, more preferably 500 to 5,000 Pa. The suction force is measured with a Manostar gauge attached inside the box of the suction conveyor. The coating material containing the above described components is continuously applied to, for example, a side of a continuous-length base sheet. Any known coating technique may be used, such as roller coating, die coating, screen printing, gravure coating, knife coating, or contour coating. Die coating is preferred in view of ease of coating, ease of controlling the coating build-up, and uniform application of the coating material.

(4-2) Electrolyte Addition Step

The electrolyte addition step of the method 4 is characterized in that an electrolyte is added in a solid state. The electrolyte is added apart from oxidizable metal particles and water. The electrolyte may be added along with other solid component except oxidizable metal particles, such as encapsulated flavor component, but is preferably added alone. In the latter case, any other solid component is compounded into the coating material described above. To add the electrolyte alone is effective in improving the dispersibility of the other solid component in the heat generating layer. As compared with adding the electrolyte in the form of an aqueous solution, adding the electrolyte in a solid state is effective in suppressing corrosion of the equipment as well as suppressing splashing of the electrolyte onto the equipment and/or surroundings.

The form of the electrolyte is not limited as long as it is added in a solid state. For example, it may be granules with visually observable sizes or visually unobservably small particles. In order for the electrolyte to smoothly dissolve into the coating layer formed by applying the coating material, the electrolyte is preferably added in the form of powder as agglomerates of microfine particles. For example, the electrolyte is preferably added in the form of powder with an average particle size of 50 to 1000 μm, more preferably 100 to 800 μm. The average particle size is measured by, for example, a sieve method using standard sieves specified in JIS Z8801.

In the case when addition of the electrolyte is preceded by application of the coating material, it is preferred that the electrolyte be uniformly spread over the entire area of the coating layer formed in the coating step so that a heat generating layer having a uniform composition may be formed. For the same reason, in the case when addition of the electrolyte is followed by application of the coating material, it is preferred that the electrolyte be uniformly spread over the entire area of the region of the base sheet where the coating material is to be applied. In the case when the coating material and the electrolyte are simultaneously supplied to the base sheet, it is preferred that the electrolyte be uniformly added over the same region as the region to be coated with the coating material. In any case, the electrolyte may be added by means of, for example, a screw feeder, an electromagnetic feeder, an auger feeder, or the like. Note that it is only necessary for the electrolyte to come to exist uniformly in the heat generating layer by the time when the heat generating element is used. In other words, the electrolyte does not need to be added uniformly to the base sheet in the electrolyte addition step.

The electrolyte may be added once or in divided portions. In the former case, the electrolyte is added to the coating layer formed by applying the coating material, or addition of the electrolyte to the base sheet is followed by applying the coating material to form a coating layer. Addition of the electrolyte to the coating layer formed by applying the coating material may be followed by recoating with the coating material. In the case of adding in divided portions, the electrolyte may be added in two or more divided portions to the coating layer formed by applying the coating material. Otherwise, adding the electrolyte in divided portions may be followed by applying the coating material. It is also possible that addition of the electrolyte to the base sheet is followed by applying the coating material, followed by addition of the electrolyte to the coating layer.

The amount of the electrolyte to be added is preferably such that the electrolyte content in the finally obtained heat generating layer may fall within the above recited range. The amount of the electrolyte to be added is preferably 0.5 to 15 parts, more preferably 1 to 10 parts, per 100 parts by mass of the amount of the oxidizable metal particles per unit area.

In the case where the electrolyte is added to the coating layer formed by applying the coating material, the coating part and the spreading part in the apparatus are separate from each other, which is advantageous to simplify the mechanism of the apparatus. When the base sheet contains a superabsorbent polymer, there is produced another advantage: since the coated surface is in a sufficiently wetted state so that the electrolyte being spread is prevented from scattering to the surroundings. This tendency may be taken advantage of in controlling the amount of absorption by the base sheet by altering the timing of spreading the electrolyte. This is because a higher electrolyte concentration results in lower absorbency of the absorbent polymer.

In the case where, on the other hand, spreading the electrolyte to the base sheet precedes applying the coating material, there is obtained an advantage of rapid dissolution of the electrolyte for the following reason. Because the coating material is applied onto the electrolyte, the water content of the coating material passes through the electrolyte while being wicked into the base sheet.

In the case where applying the coating material and spreading the electrolyte are carried out simultaneously, the sufficient wetness of the coated surface will prevent the spread electrolyte from scattering to the surroundings.

When the coating material is applied to the base sheet before addition of the electrolyte, the water content of the base sheet (inclusive of the coating layer) after the application of the coating material and before the electrolyte addition is preferably 10% to 60%, more preferably 12% to 50%, by mass. With this water content, the coated side is sufficiently wet and capable of stably holding the electrolyte added thereon, and good warming characteristics are obtained. The water content of the heat generating element is measured by the method described supra. That is, the heat generating element is weighed in a nitrogen environment, dried in a drying oven at 105° C. in vacuo for 2 hours to be freed of water, and weighed again. The change in mass, which corresponds to the amount of water, is divided by the mass of the heat generating element before drying, and the quotient is multiplied by 100 to give a water content of the heat generating element. The above discussed water content of the heat generating element is a value obtained in the case where the base sheet has a heat generating layer on either one of its two sides.

Whether the coating step is preceded or followed by the electrolyte addition step, the electrolyte does not have to immediately dissolve in the coated layer but only has to dissolve by the time of use of the heat generating element. Therefore, it does not matter if the electrolyte remains undissolved in any processing step after completion of the coating step and the electrolyte addition step. The electrolyte added does not have to completely dissolve and may partially remain undissolved at the time of use.

In the method 4, oxidation of the oxidizable metal may commence on contact between the coating layer and the electrolyte. In order to suppress the oxidation, it is recommended to maintain the production line in a non-oxidative atmosphere.

The base sheet that can be used in the method 4 may be a fibrous sheet containing superabsorbent polymer particles and hydrophilic fibers as previously described. Beside such a fibrous sheet, other sheeting that has conventionally been used in the art is also usable. For example, an air impermeable material, such as a synthetic resin film, or air permeable material, such as nonwoven fabric or paper, is useful. A laminate of a synthetic resin film and a fibrous sheet such as nonwoven fabric is also useful. The base sheet is preferably a water absorbing sheet.

In using a fibrous sheet as the base sheet, the fibrous sheet does not need to contain superabsorbent polymer particles when it has sufficient absorbency (for example, when it is made of highly absorbent fibers) relative to the water content of the coating material.

When the heat generating layer is sandwiched in between two base sheets (one base sheet is coated with the coating material, while the other is superposed on the heat generating layer), it is preferred for either of the two base sheets to contain superabsorbent polymer particles. Both the base sheets may contain superabsorbent polymer particles.

The heat generating element obtained by forming a heat generating layer on a base sheet according to the above described method may be subjected to post-processing for the purpose of improving heat generation characteristics or handling properties of the heat generating element. For instance, the heat generating element may be covered with an air permeable enclosing material. When, for example, the heat generating element has a continuous form, the continuous-form heat generating element is cut across the length into individual heat generating elements, the individual heat generating elements are transported in one direction at a given spacing therebetween, a continuous-length first cover sheet is disposed on the heat generating layer side of the heat generating element, and a continuous-length second cover sheet is disposed on the other side. The details of these operations are the same as with the covering step (2-3) of the method 2.

In using a base sheet made of an absorbent material, e.g., the above described fibrous sheet, because the heat generating layer has its water content decreased to have reduced flowability by the absorbency of the fibrous sheet by the time when the first cover sheet is overlaid thereon, the problem of the heat generating layer sticking to the first cover sheet is avoided. As a result, the air permeability of the first cover sheet is successfully maintained.

A continuous form having a plurality of heat generating devices connected in series in one direction is thus obtained. The continuous form is cut across the length between adjacent heat generating devices to yield heat generating devices enclosed in an enclosing material. The resulting heat generating device is sealed in an oxygen-barrier package in the subsequent step.

Figure 8:
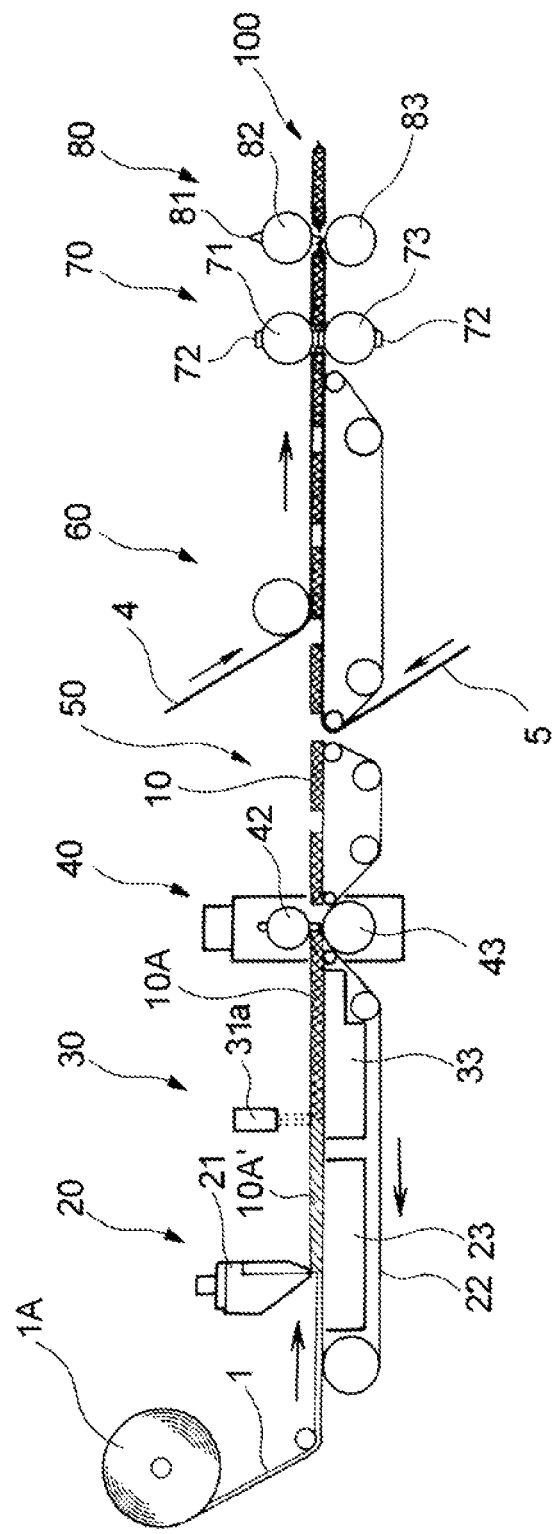
FIG. 8 is a schematic illustration of still another example of an apparatus suitably used to produce the heat generating element or device of the invention.

FIG. 8 illustrates an example of an apparatus preferably used to carry out the method 4. The apparatus includes a coating part 20, an electrolyte addition part 30, a first cutting part 40, a re-pitching part 50, a covering part 60, a sealing part 70, and a second cutting part 80. The apparatus shown is for the embodiment in which application of the coating material is followed by spreading the electrolyte.

The details of the coating part 20 are the same as of the coating part 20 of the apparatus shown in FIG. 2. A continuous-length base sheet 1 unrolled from a stock roll 1A is transported by the endless belt 22, and a coating material is applied to one side of the base sheet 1 with the die coater 21 to form a coating layer on that side. The coating material has been prepared by an unshown equipment. In the case where the base sheet is a fibrous sheet, the suction box 23 operates while the base sheet 1 is transported by the endless belt 22, thereby to stabilize the transportation and suck water in the coating material to control the amount of water to be absorbed and retained by the base sheet 1. Depending on the kind of the base sheet 1 or the composition of the coating material, the suction box 23 does not need to operate. After the coating material is applied, the water of the coating material is absorbed by the base sheet 1 so that the water content of the coating layer is lower than that of the coating material. It follows that the coating layer reduces in flowability.

The electrolyte addition part 30 includes an electrolyte spreader 31a for spreading a solid electrolyte, an endless belt 22 formed of wire mesh that faces the lips of the spreader 31a and runs in the direction indicated by the arrow, and a suction box 33 that faces the lips of the spreader 31a across the endless belt 22. After coated with a coating material, a continuous-length base sheet 1 is transported by the endless belt 22 from the coating part 20 to the electrolyte addition part 30, where a solid electrolyte 3a is spread from the spreader 31a through the lips to the coated side of the base sheet. The spread electrolyte 3a gradually dissolves in the coating layer immediately or over a prescribed period of time. While the base sheet 1 is transported through the electrolyte addition part 30, the suction box 33 may operate to stabilize the transportation.

There is thus obtained a continuous-length heat generating element 10A. The continuous-length heat generating element 10A is cut across its length in the first cutting part 40. The details of the cutting operation are the same as in the first cutting part 40 of the apparatus shown in FIG. 2.

The running pitch of the individual heat generating elements 10 is changed in the re-pitching part 50 so that they may be transported at a given spacing therebetween. The details of the re-pitching operation are the same as those of the re-pitching part 50 of the apparatus shown in FIG. 2.

The re-pitched heat generating elements 10 are forwarded to the covering part 60, where the individual heat generating elements 10 are entirely covered with a continuous-length first cover sheet 4 and a continuous-length second cover sheet 5. The details of the covering operation are the same as those of the covering part 60 of the apparatus shown in FIG. 2.

There is thus obtained a continuous form of a plurality of heat generating devices connected in one direction. The continuous form is cut across its length in the second cutting part 80. The details of the cutting are the same as those of the second cutting part 80 of the apparatus shown in FIG. 2.

Figure 9:
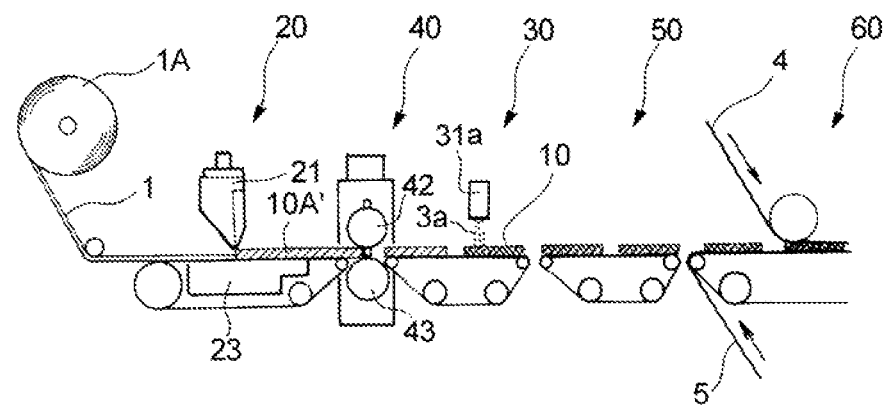
FIG. 9 is a schematic illustration of still another example of an apparatus suitably used to produce the heat generating element or device of the invention.

FIG. 9 illustrates another example of an apparatus preferably used to carry out the method 4. The apparatus of FIG. 9 is equivalent to the apparatus of FIG. 8 except that the re-pitching part 50 is differently positioned and that the electrolyte addition part 30 does not have a suction box. The apparatus of FIG. 8 has the first cutting part 40 between the electrolyte addition part 30 and the re-pitching part 50, whereas the apparatus of FIG. 9 has the first cutting part 40 between the coating part 20 and the electrolyte addition part 30. The electrolyte addition part 30 of the apparatus of FIG. 9 does not have a sucking means, like a suction box, that sucks the base sheet from the non-coated side. The apparatus of FIG. 9 has otherwise the same structure as the apparatus of FIG. 8.

Figure 10:
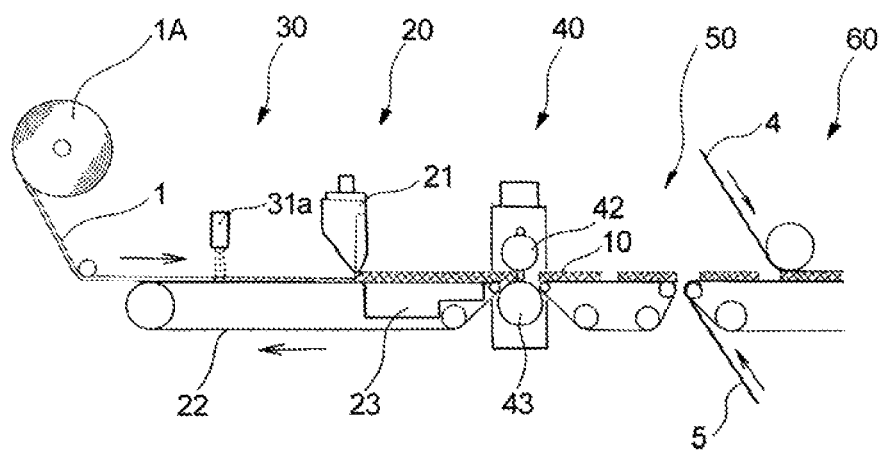
FIG. 10 is a schematic illustration of still another example of an apparatus suitably used to produce the heat generating element or device of the invention.

The apparatus shown in FIG. 10 is also preferably used to carry out the method 4. Unlike the apparatus shown in FIGS. 8 and 9, the apparatus of FIG. 10 operates to carry out the step of spreading an electrolyte before applying a coating material. The apparatus of FIG. 10 is the same as the apparatus of FIG. 8, except that the positions of the coating part 20 and the electrolyte addition part 30 are reversed. That is, the apparatus of FIG. 8 has the coating part 20 located upstream of the electrolyte addition part 30 relative to the direction of the travel of the base sheet 1, while the apparatus of FIG. 10 has the electrolyte addition part 30 located upstream of the coating part 20 relative to the direction of the travel of the base sheet 1. By the use of the apparatus shown in FIG. 10, a solid electrolyte 3a is spread on one side of the base sheet 1, and the coating material is then applied thereon to form a coating layer. The electrolyte 3a dissolves in the coating layer to form a heat generating layer.

Figure 11:
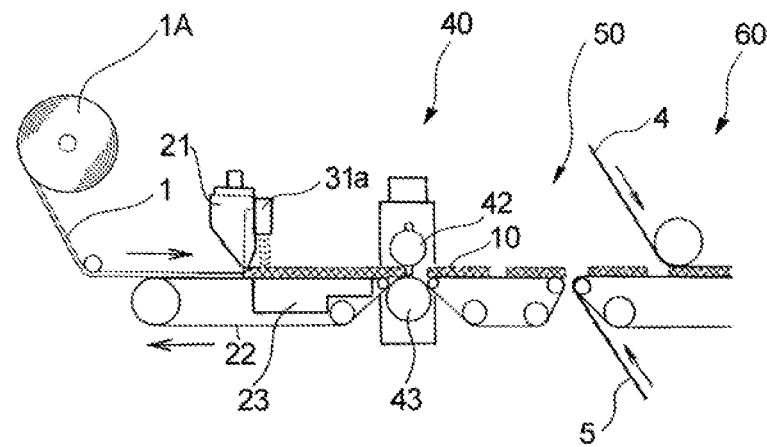
FIG. 11 is a schematic illustration of still another example of an apparatus suitably used to produce the heat generating element or device of the invention.

FIG. 11 illustrates an apparatus that is also preferably used to carry out the method 4. The apparatus of FIG. 11 has a die coater 21 for applying a coating material and an electrolyte spreader 31 integrated to each other, so that applying the coating material to the base sheet 1 and spreading the electrolyte 3a on the base sheet 1 are performed simultaneously. As used herein, the term "simultaneously" does not always mean "exactly simultaneously". Only if the step of applying the coating material and the step of spreading the electrolyte 3a are carried out by using a single unit, the two steps are regarded to be performed simultaneously even if the two steps are not conducted exactly simultaneously.

Figure 12:
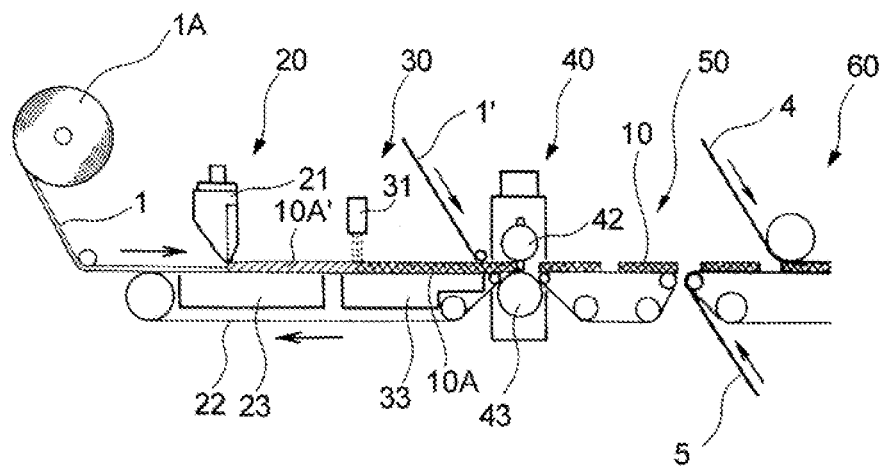
FIG. 12 is a schematic illustration of still another example of an apparatus suitably used to produce the heat generating element or device of the invention.

The apparatus shown in FIG. 12 is different from the apparatus of FIG. 8 in that a continuous-length second base sheet 1' is overlaid on the heat generating element 10A at a position between the coating part 20 and the first cutting part 40 and after adding the electrolyte at the electrolyte addition part 30. The second base sheet 1' may be the same or different from the base sheet 1. According to this method, a heat generating element having the heat generating layer sandwiched between the same or different base sheets is produced with ease. Overlaying the base sheet 1' on the heat generating element 10A may also be carried out in the apparatus shown in FIGS. 9 to 11.

Figure 13:
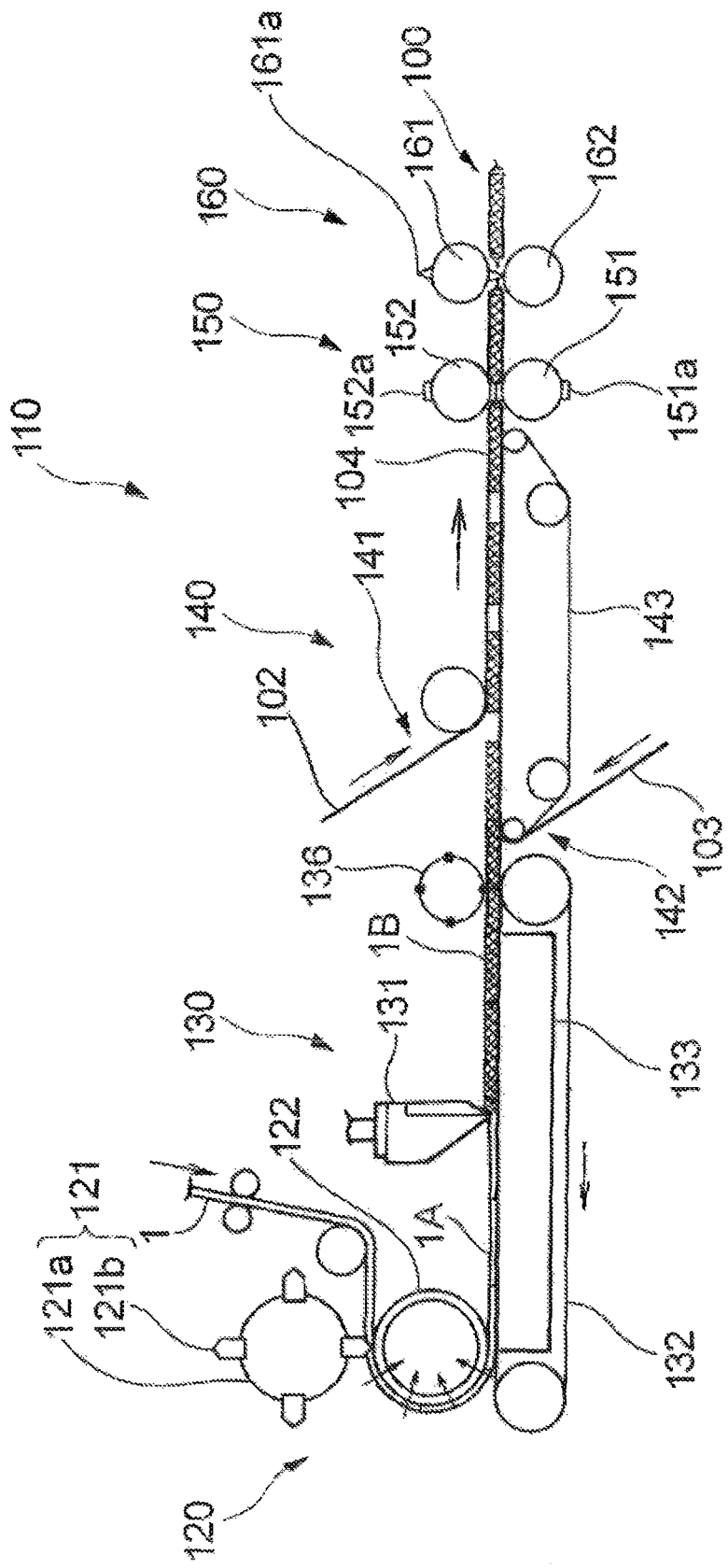
FIG. 13 is a schematic illustration of still another example of an apparatus suitably used to produce the heat generating element or device of the invention.

A method 5 described below is also useful as yet another method for making a heat generating element. While the method 5 is advantageous for making the above discussed heat generating element, it is widely applicable to the production of other than the heat generating element, such as a sheet having a coating layer formed of, for example, a viscous material. FIG. 13 schematically illustrates an example of an apparatus that is preferably used to carry out the method 5. The shown apparatus 110 includes a first cutting part 120, a coating part 130, a re-pitching part 140, a sealing part 150, and a second cutting part 160.

The cutting part 120 includes a rotary die cutter 121 and an anvil roller 122. The rotary die cutter 121 has a main roller body 121a and a plurality of cutting blades 121b attached to the periphery of the main roller body 121a. The cutting blades 121b are affixed with their width direction coincident with the axial direction of the main roller body 121a and their pointing direction coincident with the radial direction of the main roller body 121a. The anvil roller 122 has a smooth peripheral surface. The anvil roller 122 has inside a cavity extending in the axial direction which is connected to an unshown evacuator. The anvil roller 122 has unshown small holes open on its peripheral surface interconnected to the cavity. The evacuator operates to suck air from the outside into the inside of the anvil roller 122 through the holes. The rotary die cutter 121 and the anvil roller 122 are disposed with the cutting blade 121b of the former in contact with or in clearance spaced relation to the periphery of the latter.

The coating part 130 has a die coater 131, an air-permeable endless belt 132 formed of wire mesh that faces the die lips of the die coater 131 and runs in the direction indicated by the arrow, and a suction box 133 that faces the die lips of the die coater 131 across the endless belt 132.

The coating part 130 also has a coating layer separating unit 136 for separating the continuous-length coating layer formed over a plurality of the cut base sheets. The coating layer separating unit 136 may be, for example, a cylindrical member made of wire or a blade made of polytetrafluoroethylene. The coating layer continuously formed by continuous application of a coating material is cleanly cut by the coating layer separating unit 136.

The re-pitching part 140 has an endless belt 143 that runs at a higher speed than the endless belt 132 of the coating part 130. The difference in running speed allows changing the distance between cut base sheets 1B being successively transported. Any other known means for changing the pitch of moving articles may be used for re-pitching. The details of such apparatus are described, e.g., in EP 0812789 and WO 2002/007664. The re-pitching part 140 also has a joining mechanism 141 for joining a first cover, sheet and a joining mechanism 142 for joining a second cover sheet.

The sealing part 150 has a sealing roller 151 having a sealing projection 151a and a sealing roller 152 having a sealing projection 152a. The sealing rollers 151 and 152 are each heatable to a predetermined temperature. The sealing rollers 151 and 152 are disposed with their respective sealing projections 151a and 152a in contact with each other or in clearance spaced relation to each other.

The second cutting part 160 has a rotary die cutter 161 having a cutting blade 161a and an anvil roller 162. The rotary die cutter 161 and the anvil roller 162 are disposed with the cutting blade 161a of the former and the periphery of the latter being in contact with each other or in clearance spaced relation to each other.

The thus constructed method for producing a sheet having a coating layer will be described. The base sheet 1 is unrolled from an unshown stock roll and travels as a continuous length. The base sheet 1 is introduced into the first cutting part 120, where it is successively cut along a direction crossing the running direction into cut base sheets 1A. In cutting the continuous-length base sheet 1, the evacuator (not shown) connected to the anvil roller 122 of the first cutting part 120 operates to cause the anvil roller 122 to suck in air. Even after the continuous-length base sheet 1 is cut into cut base sheets 1A, the individual base sheets 1A are held by suction to the peripheral surface of the anvil roller 122 and continues traveling with no spacing between adjacent base sheets 1A.

Figure 14:
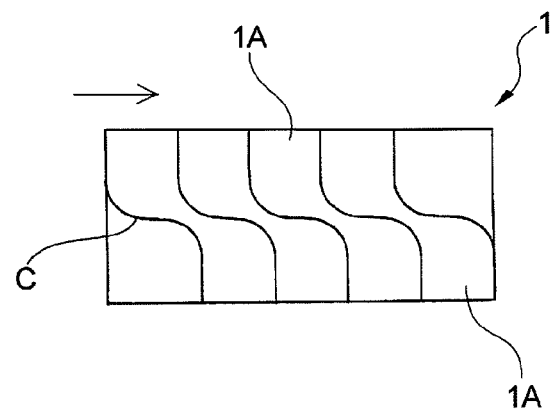
FIG. 14 shows an example of the pattern of cutting a slit in a continuous-length base sheet.

The cutting of the continuous-length base sheet 1 is done along a cutting line generally extending in the transverse direction of the base sheet 1. For example, the cutting line may be straight across the base sheet 1, or the cutting line may be curved like the cutting line C shown in FIG. 14. In either case, the cutting pattern is preferably such that does not produce waste trimmings.

The cut base sheets 1A are introduced from the first cutting portion 120 to the coating part 130 and transferred to the endless belt 132 of the coating part 130. The transfer of the base sheets 1A to the endless belt 132 is achieved smoothly because the endless belt 132 is air permeable, the suction box 133 opposite to the base sheets 1A across the endless belt 132 operates, and the running speed of the endless belt 132 is the same as the rotational speed of the anvil roller 122. Therefore, after the transfer to the endless belt 132, the individual base sheets 1A continue running in tight line (with no spacing between adjacent base sheets 1A).

In the coating part 130, a viscous material as a coating material is applied to the surface of the base sheets 1A. The term "viscous material" as used herein refers to a type of fluids and broadly includes fluent substances, such as paints, gels, slurries, creams, inks, and dough. The above described heat generative composition also comes under the term "viscous material". The coating material may be applied to the entire surface of the base sheets 1A or other than the edge portion(s) of the base sheets 1A extending in the running direction. The coating material may also be applied in stripe pattern extending in the running direction of the base sheets 1A. Since the individual base sheets 1A are tightly lined up in the running direction with no space therebetween, the coating material, even when applied continuously, does not smear the apparatus 110, typically the endless belt 132. That is, the viscous coating material is allowed to be continuously applied to the base sheets 1A.

When the viscous material is, for example, a slurry having powder dispersed in a liquid medium, the viscosity of the slurry is preferably 500 to 20,000 mPa·s, more preferably 1,000 to 10,000 mPa·s. The viscosity is measured in an environment of 23° C. and 50% RH using, for example, a Brookfield viscometer (e.g., BII viscometer BHII, from Told Sangyo Co., Ltd.) equipped with a No. 4 rotor at a rotor speed of 6 to 20 rpm.

When the viscous material is dough, the viscosity of the dough is preferably 3,000 to 300,000 mPa·s at a shear rate of $10\ s^{-1}$ and 60 to 20,000 mPa·s at a shear rate of $1000\ s^{-1}$. As used herein, the term "dough" denotes, as described, e.g., in commonly assigned US2002/001325A1, a material obtained by kneading a powdery composition with a fluid, such as a liquid, a paste, or a gel. The term "fluid" includes a substance that is fluidized on heating, pressure application, or shearing. The viscosity of dough is measured in an environment of 23° C. and 50% RH using, for example, a rotational Couette-type viscometer Rotovisco RV20 from HAAKE having a concentric cylinder geometry having an inner cylinder diameter of 19.2 mm, an outer cylinder diameter of 23.1 mm with a gap of 1.9 mm and an inner cylinder length of 31.95 mm.

When the viscous material is a gel, for example, a water-containing gel used in a cosmetic sheet, etc., the viscosity of the gel is preferably 400,000 to 1,300,000 mPa·s. The viscosity is measured in an environment of 23° C. and 50% RH using, for example, a rotational viscometer TV-10R from Toki Sangyo equipped with a T-bar spindle (T-bar stage: TX-10) under conditions of a rotational speed of 5 rpm, a measuring time of 1 minute, and a stage rising speed of 20 mm/min.

During applying the coating material, the suction box 133 facing the die coater 131 operates to conduct suction. When the base sheet 1A is air permeable, like a fibrous sheet, the suction allows for stable application of the coating material to the base sheet 1A to form a stable coating layer.

In this way, a coating material which is a viscous material is applied to one side of the base sheet 1A to form a coating layer. In what follows, the cut base sheet 1A having the coating layer is called a coated sheet 1B. The coated sheets 1B run with no space therebetween and enter the re-pitching part 140, where the distance between the running adjacent coated sheets 1B is increased to create a spacing therebetween. The spacing is decided according to the setup condition of the re-pitching unit.

Prior to increasing the distance between the coated sheets B1, it is preferred to cleanly cut the coating layer between adjacent coated sheets 1B by the use of the coating layer separating unit 136 to help achieving smooth re-pitching. By this operation, the coating layer of the viscous material is effectively prevented from threading or stringing. When the coating material is not stringy, there is no need to provide the coating layer separating unit 136.

In the re-pitching part 140, not only are the tightly lined up coated sheets 1B spaced away from each other, but a continuous-length first cover sheet 102 and a continuous-length second cover sheet 103 are joined to the upper surface (e.g., the coated side) and the lower surface of the coated sheets 1B, respectively. There is thus formed a laminate 104 having the individual coated sheets 1B between the first cover sheet 102 and the second cover sheet 103. The laminate 104 is a continuous-length having the coated sheets 1B spacedly disposed.

It is preferred for each of the first cover sheet 102 and the second cover sheet 103 to have a width enough to provide an extended portion extending transversely outward from each lateral side edge of the coated sheet 1B. By providing the extended portions, the coated sheet 1B is successfully sealed between the cover sheets 102 and 103 in the sealing portion 150.

The first and the second cover sheet 102 and 103 may be paper, nonwoven fabric, film, a laminate thereof, and so forth. For example, an air permeable or impermeable resin film may be used. The material of the cover sheets is not limited to the above and may be selected appropriately according to the intended use of the product. When in making the heat generating device 100 shown in FIG. 3 by the method 5, it is preferred that at least one of the first and the second cover sheet 102 and 103 be air permeable.

The laminate 104 is introduced into the sealing part 150, where the extended portions of the first cover sheet 102 and the second cover sheet 103 extending outward from each coated sheet 1B are bonded together by a prescribed bonding means. The bonding is effected outside the opposite lengthwise edges and the opposite transverse edges of each coated sheet 1B by, for example, fusion bonding, ultrasonic bonding, or adhesion with an adhesive. Since adjacent coated sheets 1B have been spaced in the re-pitching part 140 as earlier discussed, sufficient regions for bonding the two cover sheets 102 and 103 outside the opposite lengthwise edges of each coated sheet 1B are secured.

The bonding in the sealing part 150 is preferably performed in such a manner as to form a closed bonded portion continuously surrounding each coated sheet 1B. The bonded portion may be either continuous to hermetically seal the coated sheet 1B by the two cover sheets 102 and 103 or discontinuous.

The thus sealed laminate 104 is forwarded to the second cutting part 160, where it is cut across it length between every adjacent pair of coated sheets 1B to produce a desired product, such as the heat generating device 100.

Unlike the technique disclosed in patent literature 2, the above discussed method includes the step of cutting the base sheet 1 before applying the coating material that is a viscous material and therefore provides an effective solution to the problem that a coating material adheres to the cutting blade. As a result, the blade is effectively prevented from rusting, and the sharpness of the blade lasts long, enabling stable production for a prolonged period of time.

Figure 15:
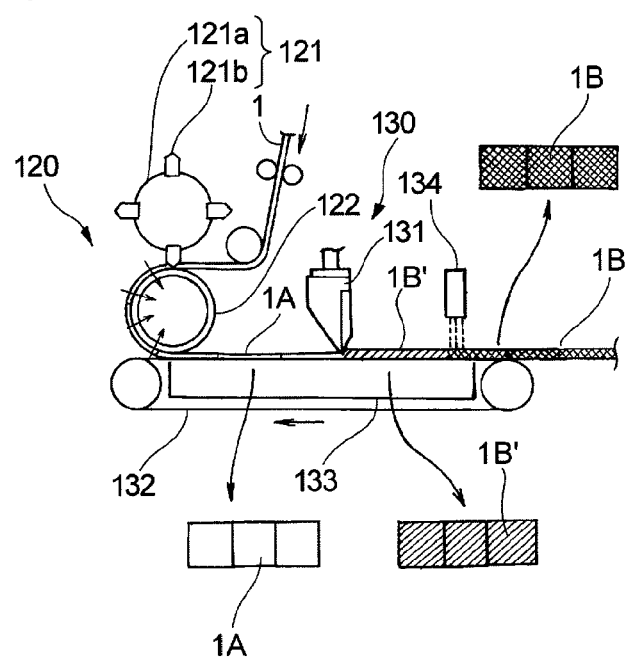
FIG. 15 is a schematic illustration of yet another example of an apparatus suitably used to produce the heat generating element or device of the invention.

FIG. 15 illustrates a modification of the apparatus shown in FIG. 13. The apparatus 110 shown in FIG. 15 has a nozzle 134 downstream from the die coater 131 in the coating part 130. This apparatus is effective in the cases when the coating material that is a viscous material is unstable, for example, when the components contained in a coating material can react with each other and must be separated from each other to be kept from reacting. When, for example, components A and B contained in a coating material are reactive with each other, these components may be separated from each other by separately preparing (A) a coating material precursor containing the component A but free from the component B and (B) a liquid containing the component B. The coating material precursor (A) is applied to the cut base sheet 1A using the die coater 131 to form a coated sheet precursor 1B'. The component B-containing liquid (B) is then added dropwise to each cut base sheet 1A. The component B may be dropwise added discontinuously to the re-pitched and spaced base sheets 1B. Alternately, the positions of the die coater 131 and the nozzle 134 in the apparatus shown in FIG. 15 may be reversed. In this case, dropwise addition of the component B-containing liquid from the nozzle 134 to the cut base sheets 1A is followed by applying the coating material precursor to the cut base sheets 1A using the die coater 131. In the apparatus of FIG. 15, the structure downstream from the coating part 130 is equal to that of the apparatus shown in FIG. 13.

FIG. 16 illustrates another apparatus 110 that can be used to carry out the method 5. The difference of this apparatus from that of FIG. 13 is the structure of the rotary die cutter 121 in the cutting part 120 as will be described below in detail.

Figure 17A:
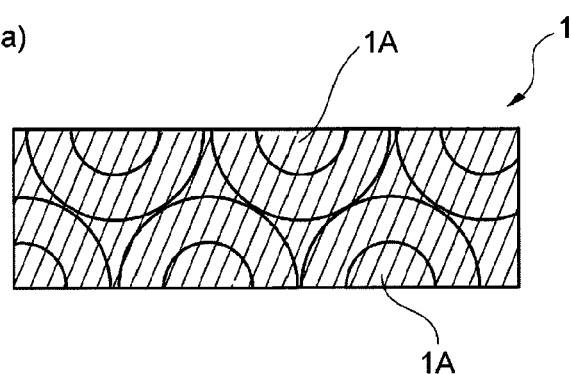
FIG. 17(a) shows an example of the pattern of cutting a slit in a continuous-length base sheet.

A base sheet 1 unrolled from a unshown stock roll travels as a continuous length. The base sheet 1 is introduced into the first cutting part 120. In the first cutting part 120, slits of closed pattern 105 is successively made in the continuous-length base sheet 1 so as to form a plurality of cut base sheets 1A lined up in the running direction of the base sheet 1. The slit 105 is a continuous line. FIG. 16 shows an embodiment (101) in which slits 105 is made in oval with its major axis coincident with the running direction of the base sheet 1. The blade affixed to the rotary die cutter 121 has a shape corresponding to such a shape of the slit 105. In cutting the continuous-length base sheet 1, the evacuator (not shown) connected to the anvil roller 122 of the first cutting part 120 operates to cause the anvil roller 122 to suck in air. Even after the slit 105 is cut in the continuous-length base sheet 1 to make the cut base sheets 1A, the individual base sheets 1A are held by suction to the peripheral surface of the anvil roller 122 and continues traveling without separating from the continuous-length base sheet 1. In the method shown in FIG. 16, the slit of closed pattern 105 may be replaced with slits of other patterns, for example, the slits shown in FIG. 17(a) as will be discussed later.

The continuous-length base sheet 1 is transported from the first cutting part 120 to the coating part 130 without having the cut base sheets 1A separated therefrom and transferred to the endless belt 132 of the coating part 130. By the action of the suction box 133 installed in the coating part 130, the continuous-length base sheet 1 and the cut base sheets 1A are smoothly transferred to the endless belt 132. Accordingly, after the transfer to the endless belt 132, the cut base sheets 1A continue running without being separated from the continuous-length base sheet 1.

In the coating part 130, a coating material that is a viscous material is applied to at least the entire area of the cut base sheets 1A. The coating material is preferably applied with a coating width exceeding the largest width of the cut base sheets 1A so that every cut base sheet 1A may certainly be coated with the coating material on its entire area even if the continuous-length base sheet 1 runs in a zig-zag motion.

Since in the coating part 130 the cut base sheets 1A are not separate from the continuous-length base sheet 1, i.e., there is no space between every cut base sheet 1A and the continuous-length base sheet 1, the coating material, even when applied continuously, does not smear the apparatus 110, typically the endless belt 132.

Figure 17B:
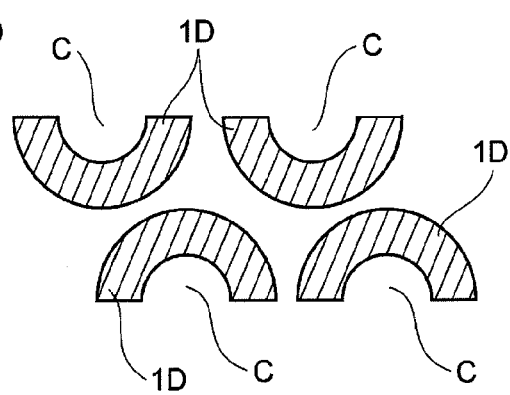
FIG. 17(b) illustrates the remainder left after separating and discarding cut pieces from the slit base sheet.

In using the apparatus shown in FIG. 16, the pattern of making slits in the continuous-length base sheet 2 may be the pattern shown in FIG. 17(*a*), in which case a plurality of cut base sheets 1A and a plurality of cut base sheets 1D are formed. In this case, the cut base sheets 1A are unwanted products but are to be separated and discarded. Target products are the base sheets 1D each having a cutaway C corresponding to each cut base sheet 1A as shown in FIG. 17(*b*).

The cut base sheets 1A having the coating layer (hereinafter called coated cut sheets 1B) are separated from the continuous-length base sheet 1 having the coating layer (hereinafter called a continuous coated sheet 1C) before they enter the re-pitching part 140. In detail, the coating part 130 has a transfer pad 135 at the downstream end thereof, and the transfer pad 135 operates to stamp out the coated cut sheets 1B from the continuous coated sheet 1C so that only the coated cut sheets 1B are introduced into the re-pitching part 140. The continuous coated sheet 1C left after separating the coated cut sheets 1B is discharged out of the production line. The steps following the re-pitching step are the same as with the apparatus of FIG. 13. The structure of the apparatus 110 of FIG. 16 downstream from the coating part 130 is the same as that of the apparatus of FIG. 13.

In the case of the slit pattern shown in FIG. 17(*a*), a plurality of coated cut sheets 1A are separated and discarded to leave a plurality of coated cut sheets 1D (see FIG. 17(*b*)) which are target products. Each coated cut sheet 1D has a cutaway C corresponding to each coated cut sheet 1A. The separation of the cut coated sheets 1A may be achieved using a suction device (not shown). The coated cut sheets 1D may be re-pitched, if desired.

FIG. 18 illustrates a modification of the apparatus shown in FIG. 16. The apparatus 110 shown in FIG. 18 has a nozzle 134 downstream from the die coater 131 in the coating part 130. This apparatus is equivalent to the above-discussed apparatus of FIG. 15. In the apparatus, a coating material precursor is applied to a continuous-length base sheet 1 and cut base sheets 1A using the die coater 131, and another liquid is then added dropwise thereto using the nozzle 134. While in FIG. 18 another liquid is dropwise added before the coated cut sheets 1B are separated, the dropwise addition may be discontinuously done after the coated sheets 1B are separated.

Alternately, the positions of the die coater 131 and the nozzle 134 in the apparatus of FIG. 18 may be reversed so that dropwise addition of the liquid from the nozzle 134 is followed by application of the coating material precursor using the die coater 131. In the apparatus of FIG. 18, the structure downstream from the coating part 130 is equal to that of the apparatus shown in FIG. 13.

In carrying out the method 5 by the use of any of the apparatus shown from FIGS. 13 through 18, the base sheet may be any sheeting made of a material suited to the intended use of the final product, including the above-mentioned fibrous sheet containing superabsorbent polymer particles and hydrophilic fibers. Examples of useful sheeting are fibrous sheets, such as paper, woven fabric, knitted fabric, and nonwoven fabric; resin film or metal foil; and laminates thereof. In particular, using a base sheet having liquid absorbency provides an advantage that a liquid content of a coating material is absorbed by the base sheet to form a coating layer with improved fixability to the base sheet. It is especially ideal for the coating layer formed by the method 5 to contain a powder component in a uniformly dispersed state with a residual water content appropriate to the nature of the product. It is also desirable for the coating layer to be formed with its powder component entangled in the fibers of the base sheet so as to prevent the powder component from moving to localize in the product during use. The coating layer in the final product has such a composition that is not flowable. If a coating material having the same composition as that of the coating layer in the final product is used, it could not be applied in a stable manner. Therefore, the coating material must be diluted with a liquid to reduce its viscosity to a level suited to be applied. However, the so diluted coating material would only provide a coating layer having reduced product qualities on account of the high liquid content. If this is the case, the inconvenience is less likely to occur when in using a liquid absorbent base sheet. From these considerations, it is preferred to use a fibrous sheet having high liquid absorbency and good fixing properties for the coating layer. Paper or nonwoven fabric is particularly preferred. In using a fibrous sheet, a water soluble component is absorbed by the fibrous sheet, and the coating layer loses viscosity. This helps the coated cut sheets 1B to be separated apart.

The fiber sheet used as the base sheet in the method 5 may be made either of natural fiber and synthetic fiber. When in using hydrophilic fibers to construct the base sheet, hydrogen bonds are easily formed with the oxidizable metal contained in the heat generating layer to improve the shape retention of the heat generating layer. Using hydrophilic fibers is also advantageous in that the water absorbency and retentivity of the base sheet are improved to make it easier to control the water content of the heat generating layer. From these viewpoints it is preferred to use cellulose fiber as hydrophilic fiber. The cellulose fiber may be chemical (synthetic) fiber or natural fiber.

The viscous material that can be used in the method 5 is not particularly limited and may be any material appropriate to the intended use of the product. Examples of useful viscous materials include those containing no solid matter, such as emulsions, viscous oils, water-containing gels, dye-based inks, resin coating materials, waxes, hot-melt materials, and liquid detergents; and those containing solid matter, such as pigment-based inks, magnetic coating materials, electrically conductive coating materials, insulating coating materials, powder detergent having been rendered viscous, and oxidizable metal particles having been rendered viscous by mixing with water or gel. Considering that the method 5 is particularly effective in preventing reduction of cutting performance of the cutting blade, the advantage of the method 5 is especially pronounced when in using a viscous material containing solid matter.

One example of the solid-containing viscous material is a heat generative composition containing oxidizable metal particles, an electrolyte, and water. The heat generative composition may further contain a reaction accelerator. The material may also contain a thickener or a surfactant to improve dispersibility of the solid matter. The viscous material containing these components is applied directly to the surface of a base sheet to form a coating layer, thereby providing a heat generating element of sheet form. When the base sheet has liquid absorbency, the liquid content of the viscous material applied thereto is absorbed by the base sheet simultaneously with applying the viscous material. It follows that the viscous material reduces in viscosity, and the coating layer loses viscosity. When a first cover sheet 102 is disposed on the coating layer in the re-pitching part 140, the coating layer is effectively prevented from sticking to the first cover sheet 102. When the first cover sheet 102 is an air-permeable sheet (e.g., a porous and moisture-permeable sheet made of a synthetic resin), the sheet is less likely to be clogged by the solid matter and is effectively prevented from reducing its air permeability. When a liquid absorbent sheet is used as a base sheet, and the sheet is sucked by the suction box 133 during applying the viscous material, the wicking of the liquid of the viscous material into the base sheet is accelerated, which is more effective in rapidly reducing the viscosity of the coating layer.

In preparing the heat generative composition as a viscous material, if the oxidizable metal particles, electrolyte, and water co-exist in the composition, oxidation of the oxidizable metal particles can be accelerated. Therefore, it is advantageous that the oxidizable metal particles and the electrolyte are separated from each other. From this viewpoint, in the case of using the above described heat generative composition as a viscous material, it is preferred to use the apparatus of FIG. 15, in which a composition containing oxidizable metal particles and water but not containing an electrolyte is applied as a viscous material to the cut base sheets 1A, and an aqueous solution of the electrolyte is added to the coated base sheets 1A before increasing the distance between the coated base sheets 1A. It is also preferred that the aqueous electrolyte solution be added to the cut base sheets 1A after cutting the continuous-length base sheet 1 and before applying the viscous material.

When oxidizable metal particles and an electrolyte should be separated, the apparatus shown in FIG. 18 is also useful in place of the apparatus of FIG. 15. In this case, it is preferred that a composition containing oxidizable metal particles and water but not containing the electrolyte is applied as a viscous material to the continuous-length base sheet 1, and an aqueous solution of the electrolyte is added to the coated continuous-length base sheet 1 before separating the coated cut base sheets 1A from the coated continuous-length base sheet 1. It is also preferred that the aqueous electrolyte solution be added to the continuous-length base sheet 1 after making the slits 105 and before applying the viscous material.

While the apparatus shown in FIGS. 13 through 18 useful in carrying out the method 5 have a die coater for applying a coating material that is a viscous material, other coating means may be used as well, such as roller coating, screen printing, gravure coating, knife coating, or contour coating.

The apparatus shown in FIG. 15 may have the same means as the coating layer separating unit 136 shown in FIG. 13 at a position upstream from the step for separating the individual cut base sheets 1A from the continuous-length base sheet 1. Similarly, the apparatus shown in FIGS. 16 and 18 may have the same means as the coating layer separating unit 136 shown in FIG. 13 at a position before the step for separating the individual base sheets 1A from the continuous-length base sheet 1 and also upstream from the transfer pad 135.

EXAMPLES

The present invention will now be shown in greater detail with reference to Examples, but it should be understood that the scope of the invention is not limited thereto. Unless otherwise noted, all the percents and parts are by mass.

Example 1

(1) Preparation of Heat Generative Composition as Coating Material

A heat generative composition as a coating material was prepared from 100 parts of iron powder with an average particle size of 45 µm as an oxidizable metal, 8 parts of activated carbon with an average particle size of 42 µm as a reaction accelerator, 3 parts of sodium chloride as an electrolyte, 0.2 parts of guar gum as a thickener, 0.25 parts of a carboxylic acid type polymeric surfactant as a surfactant, and 60 parts of water. The resulting coating material had a viscosity of 4,500 mPa·s as measured using a Brookfield viscometer equipped with a No. 4 rotor in an environment of 23° C. and 50% RH.

(2) Preparation of Base Sheet

A sheet depicted in FIG. 19 was used as a base sheet. The base sheet 1 was prepared in accordance with the method taught in JP 8-246395A. The base sheet 1 is a one-ply sheet containing sodium polyacrylate-based superabsorbent polymer particles 12 predominantly in its middle portion in the thickness direction and containing substantially no superabsorbent polymer particles 12 on both surfaces thereof. The base sheet 1 had a pair of layers 11 and 13 each made of hydrophilic crosslinked bulky cellulose fibers 11a, between which the superabsorbent polymer particles 12 were sandwiched. The crosslinked bulky cellulose fiber 11a had a fiber coarseness of 0.22 mg/m and an average fiber length of 2.5 mm. Both the layers 11 and 13 of the crosslinked bulky cellulose fibers 11a contained softwood bleached kraft pulp and PVA as a strengthening agent. The superabsorbent polymer particles had an average particle size of 340 µm. The basis weight of the layer 11 was 30 g/m$^2$, and that of the layer 13 was 20 g g/m$^2$. The amount of the superabsorbent polymer particles was 30 g/m$^2$. Accordingly, the basis weight of the base sheet was 80 g/m$^2$.

(3) Making of Heat Generating Element and Heat Generating Device

A heat generating element was made in accordance with the method 1 described supra using the apparatus shown in FIG. 2. The coating material prepared above was applied to one side of the base sheet prepared above to a coating weight of 1,300 g/m$^2$ to form a continuous-length heat generating element 10A. The heat generating element 10A was cut across the length to give a heat generating element 10 in the form of cut square sheet measuring 50 mm by 50 mm.

The heat generating element 10 was entirely covered with a first cover sheet 4 and a second cover sheet 5, the first cover sheet 4 covering the side having the heat generating layer, and the second cover sheet 5 covering the other side having no heat generating layer. The extensions of the first and the second cover sheet 4 and 5 extending outward from the opposite lengthwise edges and the opposite transverse edges of the heat generating element 10 were bonded together by heat sealing to form a hermetic bonded portion continuously surrounding the heat generating element 10 with a sealing width of 5 mm. There was thus obtained a heat generating device 100 having the structure shown in FIG. 3.

The first cover sheet 4 was a polyethylene porous sheet having a basis weight of 50 g/m$^2$ and an air permeability of 2,500 s/(100 ml·6.42 cm$^2$). The second cover sheet 5 was a polyethylene air-impermeable sheet having a basis weight of 30 g/m$^2$. Each of the first and the second cover sheet 4 and 5 had a rectangular shape measuring 65 mm by 65 mm.

A micrograph of a vertical cross-section of the heat generating element 10 is shown in FIG. 20(*a*). The heat generating layer of the heat generating element 10 had a water content of 21% as measured by the method described supra. The water content of the heat generating element was 35%. The side of the heat generating element having no heat generating layer had a water content of 17%.

The resulting heat generating device 100 was evaluated for temperature characteristics in accordance with JIS S4100 (disposable body warmer test method using a warming device for determining temperature characteristics). The heat generating device 100 was put in a bag made of needle-punched nonwoven fabric having a basis weight of 100 g/m² and placed on a constant-temperature warming device set at 40° C. The bag was formed by sealing three sides of two sheets of the needle-punched nonwoven fabric. A thermometer was disposed between the heat generating device 100 and the surface of the warming device. The heat generating device 100 was disposed with the heat generating layer side up (facing opposite to the thermometer). As a result, the temperature reached the maximum of 62° C. in 15 minutes from the start of the measurement.

Separately, the heat generating device 100 was attached to the human skin for 30 minutes, and the amount of powder fallen off the heat generating layer was measured to calculate the ratio of the fallen powder as follows. The heat generating device 100 was attached to an arm using a holder. The powder remaining in the space defined by the first and the second cover sheet and the powder adhering to these cover sheets were collected and weighed. As a result, the ratio of the fallen powder was 1.3%, proving that the heat generating element is less likely to suffer from fall-off. The ratio (%) of the fallen powder was calculated from (mass of fallen powder/mass of heat generating element after use)×100.

The amount of steam released from the side of the first cover sheet 4 of the heat generating device 100 was measured by the method described supra and found to be 0.19 mg/(cm²·min). The three-point bending load of the heat generating device 100 was measured by the method described supra and found to be 0.40 N/65 mm before the onset of heat generation and 1.21 N/65 mm after the end of heat generation.

Example 2

A heat generating device was made in the same manner as in Example 1, except that a base sheet 1' of the same kind as the base sheet 1 was superposed on the coated side of the base sheet 1 having been coated with the coating material as shown in FIG. 4 to obtain a heat generating element. The resulting heat generating device was evaluated in the same manner as in Example 1. The results obtained are shown in Table 1 below.

Example 3

A heat generating device was obtained in the same manner as in Example 1, except that the amount of the coating material to be applied to the base sheet 1 was reduced to 700 g/m². The resulting heat generating device was evaluated in the same manner as in Example 1. The results obtained are shown in Table 1 below.

Example 4

A heat generating element was obtained in the same manner as in Example 1, except that pulp paper having a basis weight of 50 g/m² was superposed as another base sheet on the coated side of the base sheet 1 having been coated with the coating material. The pulp paper had a smooth surface and did not contain superabsorbent polymer particles. The heat generating layer of the heat generating element had its side facing the base sheet partly embedded in the base sheet while having the other side facing the pulp paper not embedded in the pulp paper. The resulting heat generating element was further processed in the same manner as in Example 1 to obtain a heat generating device. The heat generating device was evaluated in the same manner as in Example 1. The results obtained are shown in Table 1 below.

Comparative Example 1

A heat generating device was obtained in the same manner as in Example 1, except that the non-coated side of the heat generating element 10 and the inner side of the second cover sheet 5 were bonded with an adhesive. The adhesive was applied to the entire area of the facing side of the two members to a coating weight of 30 g/m². The resulting heat generating device was evaluated in the same manner as in Example 1. The results obtained are shown in Table 1 below.

Comparative Example 2

A heat generating device was obtained in the same manner as in Example 1, except for using pulp paper having a basis weight of 150 g/m² as a base sheet. The pulp paper had a smooth surface and did not contain superabsorbent polymer particles. The resulting heat generating device was evaluated in the same manner as in Example 1. The results obtained are shown in Table 1 below. A micrograph of a vertical cross-section of the heat generating element is shown in FIG. 20(*b*).

Comparative Example 3

Megurism® Steam Hot Eye Mask (from Kao Corp.) was evaluated in the same manner as in Example 1. The results obtained are shown in Table 1 below.

TABLE 1

|  |  | Example 1 | Example 2 | Example 3 | Example 4 | Compara. Example 1 | Compara. Example 2 | Compara. Example 3 |
|---|---|---|---|---|---|---|---|---|
| Highest Temperature (° C.) | | 62 | 67 | 61 | 65 | 62 | 59 | 58 |
| Time Required to Reach Highest Temperature (min) | | 15 | 10 | 5 | 14 | 15 | 23 | 6 |
| Three-Point Bending Load (N/65 mm) | Before Onset of Heat Generation | 0.40 | 0.75 | 0.20 | 0.28 | 0.46 | 0.29 | 0.14 |
| | After End of Heat Generation | 1.21 | 1.24 | 0.22 | 1.17 | 2.10 | 1.85 | 1.27 |
| Change in Three-Point Bending Load (%) | | 203 | 65 | 10 | 318 | 357 | 538 | 807 |
| Ratio of Fallen Powder (%) | | 1.3 | 0.3 | 0.6 | 0.2 | 4.0 | 2.2 | — |
| Amount of Released Steam (mg/(cm² · min)) | | 0.19 | 0.23 | 0.15 | 0.22 | 0.18 | 0.03 | 0.17 |

As is apparently seen from the results shown in Table 1, the heat generating devices obtained in Examples reach the highest temperature in short times, show small increase in three-point bending load after the end of heat generation, which indicates small reduction in flexibility after the end of heat generation, and suffer only small fall-off of the heat generative composition from the heat generating layer. Although the heat generating device of Comparative Example 1 reaches the highest temperature in a short time, it shows a large increase in three-point bending load after the end of heat generation, indicating loss of flexibility after the end of heat generation, and suffers considerable fall-off of the heat generating composition from the heat generating layer. The heat generating device of Comparative Example 2 needs a long time to reach the highest temperature, has a low reachable temperature, shows a large increase in three-point bending load after the end of heat generation, indicating loss of flexibility after the end of heat generation, and suffers considerable fall-off of the heat generating composition from the heat generating layer.

Comparison between FIGS. 20(a) and 20(b) reveals that the heat generating layer of Example 1 has its lower portion embedded in the base sheet whereas, in contrast, such embeddability is not observed with the heat generating layer of Comparative Example 2. For the heat generating layer to have its lower portion embedded in the base sheet is considered to contribute to minimizing the reduction in flexibility of the heat generating device after the end of heat generation.

Example 5

(1) Preparation of Coating Material and Aqueous Electrolyte Solution

A coating material was prepared from 100 parts of iron powder with an average particle size of 45 µm as an oxidizable metal, 8 parts of activated carbon with an average particle size of 42 µm as a reaction accelerator, 0.2 parts of guar gum as a thickener, 0.2 parts of a carboxylic acid type polymeric surfactant as a surfactant, and 60 parts of water. The resulting coating material had a viscosity of 6,500 mPa·s as measured using a Brookfield viscometer equipped with a No. 4 rotor in an environment of 23° C. and 50% RH. Separately, a 5% aqueous solution of sodium chloride, as an aqueous electrolyte solution, was prepared.

(2) Preparation of Base Sheet

A sheet depicted in FIG. 19 was used as a base sheet. The base sheet 1 was the same as used in Example 1.

(3) Making of Heat Generating Element and Heat Generating Device

A heat generating element was made in accordance with the method 2 described supra using the apparatus shown in FIG. 6. The coating material prepared above was applied to one side of the base sheet having a continuous length to a coating weight of 1,150 g/m². During the application, the base sheet was sucked from the other side thereof to an extent that did not draw water of the coating material to the other side. The continuous-length base sheet was then cut across the length, and the aqueous electrolyte solution was dropped through the dropping nozzle onto the coated side of the cut base sheet to make a heat generating element 10. During the addition of the aqueous electrolyte solution, the base sheet was not sucked from its non-coated side. The aqueous electrolyte solution was spread in an amount of 80 g/m². The resulting heat generating element had a square shape measuring 50 mm by 50 mm.

The resulting heat generating element 10 was entirely covered with a first cover sheet 4 and a second cover sheet 5 in the same manner as in Example 1.

The first cover sheet 4 and the second cover sheet 5 were the same as those used in Example 1.

The water content measurement was made by the method described supra. The water content of the sheet 10A' having a coating layer obtained after applying the coating material and before adding the aqueous electrolyte solution was 28% (inclusive of the water content of the coating layer). After adding the aqueous electrolyte solution and before covering with the first cover sheet 4, the water content of the heat generating element 10 was 32%, and that of the heat generating layer of the heat generating element 10 was 8%.

The resulting heat generating device 100 was evaluated for temperature characteristics in accordance with JIS S4100 (disposable body warmer test method using a warming device for determining temperature characteristics). The details of the measurement were the same as in Example 1. As a result, the temperature reached the highest temperature of 57° C. in 8 minutes from the start of the measurement.

Example 6

(1) Preparation of Aqueous Electrolyte Solution and Coating Material

The same aqueous electrolyte solution and coating material as prepared in Example 5 were used.

(2) Preparation of Base Sheet

A base sheet shown in FIG. 19 was used. The base sheet 1 was the same as used in Example 1.

(3) Making of Heat Generating Element and Heat Generating Device

A heat generating element was made in accordance with the method 3 described supra using the apparatus shown in FIG. 7. The aqueous electrolyte solution was added dropwise on one side of a continuous-length base sheet from the dropping nozzle in an amount of 80 g/m². The coating material was then applied continuously to the continuous-length base sheet on the side having received the aqueous electrolyte solution to a coating weight of 1,150 g/m². After the application, the base sheet was sucked from the opposite side to an extent that did not draw water of the coating material to the non-coated side. The continuous-length base sheet coated with the coating material was cut across the length to provide a heat generating element 10. The cut base sheet had a square shape measuring 50 mm by 50 mm.

The saturation capacity of the superabsorbent polymer for the aqueous electrolyte solution 3 to be sprayed onto one side of the base sheet 1 in the electrolyte addition part 30 was 6.9 g/10 min per part by mass of the superabsorbent polymer as measured making use of JIS K7224. The amount of the aqueous electrolyte solution 3 spread (added) was 80 g/m², which amount was larger than the value obtained by multiplying the saturation capacity of the superabsorbent polymer by the mass of the superabsorbent polymer present in the base sheet.

The amount of the coating material 2 applied to the base sheet on the side having received the aqueous electrolyte solution in the coating part 20 was 650 g/m². The suction box 23 operated while the base sheet 1 was transported in the coating part 20 to stabilize the transportation and suck the applied coating material 2.

The resulting heat generating element 10 was entirely covered with a first cover sheet 4 and a second cover sheet 5 in the same manner as in Example 1.

The first cover sheet 4 and the second cover sheet 5 were the same as those used in Example 1.

The water content measurement was made by the method described supra. The water content of the sheet 1 after the aqueous electrolyte solution addition was 65%. After applying the coating material and before covering with the first cover sheet 4, the water content of the heat generating element 10 was 40%, and that of the heat generating layer of the heat generating element 10 was 32%. The water content of the sheet 1 after the aqueous electrolyte solution addition was measured by the same method as used to measure the water content of the heat generating element.

The resulting heat generating device 100 was evaluated for temperature characteristics in accordance with JIS S4100 (disposable body warmer test method using a warming device for determining temperature characteristics). The details of the measurement were the same as in Example 1. As a result, the temperature reached the highest temperature of 58° C. in 8 minutes from the start of the measurement.

Example 7

(1) Preparation of Coating Material

The same coating material as used in Example 5 was used. The coating material was prepared by first mixing the oxidizable metal and activated carbon, and a mixture of water, the thickener, and the surfactant was added thereto, followed by mixing to uniformity.

(2) Preparation of Base Sheet

A base sheet shown in FIG. 19 was used. The base sheet was the same as used in Example 1.

(3) Making of Heat Generating Element and Heat Generating Device

A heat generating element and a heat generating device were made in accordance with the method 4 using the apparatus shown in FIG. 12. The coating material was applied to one side of the base sheet of continuous form to a coating weight of 2000 g/m$^2$. During the application, the base sheet was not sucked from the other side. Sodium chloride powder (average particle size: 425 μm) as an electrolyte was spread from the spreader 31 over the coated side of the base sheet (the side having been coated with the coating material) in an amount of 15 g/cm$^2$. Professional-quality salt Akoushio TF4 from Nihonkaisui Co., Ltd. was used as sodium chloride powder. During spreading the electrolyte, the base sheet was not sucked from the non-coated side thereof. After spreading the electrolyte, a base sheet 1' of the same kind as the base sheet 1 was superposed on the coated side as shown in FIG. 12. Both the base sheet 1 and the base sheet 1' were cut across the length to make a heat generating element 10. The resulting heat generating element 10 had a square shape measuring 50 mm by 50 mm.

The resulting heat generating element 10 was entirely covered with a first cover sheet 4 and a second cover sheet 5 in the same manner as in Example 1. The first cover sheet 4 covered the side of the second base sheet 1' of the heat generating element 10, and the second cover sheet 5 covered the side of the base sheet 1 of the heat generating element 10.

The first cover sheet 4 was a polyethylene porous sheet having a basis weight of 50 g/m$^2$ and an air permeability of 80,000 s/(100 ml·6.42 cm$^2$). The second cover sheet 5 was a polyethylene porous sheet having an air permeability of 20,000 s/(100 ml·6.42 cm$^2$). Each of the first and the second cover sheet 4 and 5 had a rectangular shape measuring 65 mm by 65 mm.

The water content measurement was made by the method described supra. The water content of the heat generating element 10 before being covered with the first cover sheet 4 was 32%, and the water content of the heat generating layer of the heat generating element 10 was 23%.

Reference Example 1

A heat generating element and a heat generating device were made in the same manner as in Example 7, except for replacing the step of spreading sodium chloride powder with the step of adding dropwise 240 g/m$^2$ of a 5% aqueous solution of sodium chloride. The heat generating element before being covered with the first cover sheet had a water content of 42%, and the heat generating layer of the heat generating element was 25%.

Figure 21:
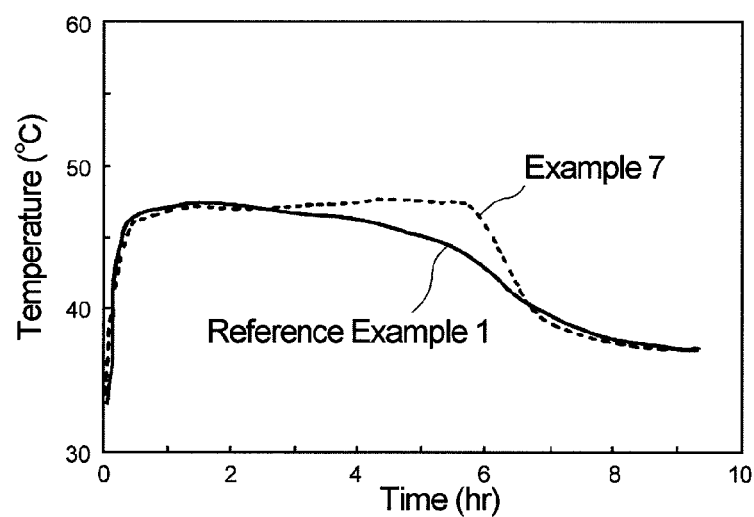
FIG. 21 is a graph showing the heat generation characteristics of the heat generating devices obtained in Example 7 and Reference Example 1.

Evaluation:

The heat generating devices obtained in Example 7 and Reference Example 1 were evaluated for temperature characteristics in accordance with JIS S4100 (disposable body warmer test method using a warming device for determining temperature characteristics). The details of the measurement were the same as in Example 1. The results obtained are shown in FIG. 21. As is apparent from the results shown, the heat generating device obtained in Example 7 has a longer duration of heat generation than the device of Reference Example 1.

The invention claimed is:

1. A heat generating device comprising a heat generating element and an enclosing material entirely enclosing the heat generating element,
   the heat generating element comprising:
   a base sheet formed of a fibrous sheet containing superabsorbent polymer particles and hydrophilic fibers, and
   a layer of a heat generative composition containing oxidizable metal particles located on a side of the base sheet,
   the enclosing material comprising a first cover sheet and a second cover sheet bonded to each other in their peripheral portions to provide a space therebetween in which the heat generating member is placed,
   the heat generating element placed in the space being in a non-fixed state to the enclosing material,
   the first cover sheet having air permeability in a part thereof and being located on the side of the layer of the heat generative composition, and
   the heat generating device being configured to release steam from the side of the first cover sheet while in use, wherein
   water being supplied from the base sheet to the heat-generative layer.

2. The heat generating device according to claim 1, wherein the second cover sheet has lower air permeability than the first cover sheet.

3. The heat generating device according to claim 1, wherein the layer of the heat generative composition is located on only one side of the base sheet.

4. The heat generating device according to claim 1, wherein the layer of the heat generative composition is located between the base sheet and another base sheet, the two base sheets being the same or different from each other.

5. The heat generating device according to claim 3, wherein the base sheet has, in its surface on which the layer of the heat generative composition is not provided, a lower water content than the layer of the heat generative composition, thereby supplying water for heat generation to the heat generating layer.

6. The heat generating device according to claim 1, wherein the heat generative composition has its lower part embedded in the base sheet.

7. The heat generating device according to claim 1, showing a change of 350% or less in three-point bending load after the end of heat generation relative to that before the onset of heat generation.

8. A method for making a heat generating element comprising:
a base sheet formed of a fibrous sheet containing superabsorbent polymer particles and hydrophilic fibers, and
a layer of a heat generative composition containing oxidizable metal particles, an electrolyte, and water located on the base sheet, wherein
water being supplied from the base sheet to the heat-generative layer,
the method comprising steps of:
applying a coating material containing the oxidizable metal particles and not containing the electrolyte to a side of the base sheet, and
adding an aqueous electrolyte solution containing the electrolyte to that side of the base sheet having the coating material applied thereto.

9. The method for making a heat generating element according to claim 8, further including the step of sucking the base sheet from the other side during applying the coating material or after applying the coating material and before adding the aqueous electrolyte solution.

10. A method for making a heat generating device comprising a step of making a heat generating element by the method according to claim 8 and a step of entirely enclosing the resulting heat generating element in an enclosing material, wherein
the step of making a heat generating element is a step of making a heat generating element having the layer of the heat generative composition in a non-flowable state, and
the step of enclosing is a step of enclosing the heat generating element having the layer of the heat generative composition in the non-flowable state in the enclosing material.

11. A method for making a heat generating element comprising:
a base sheet formed of a fibrous sheet containing superabsorbent polymer particles and hydrophilic fibers, and
a layer of a heat generative composition containing oxidizable metal particles, an electrolyte, and water located on the base sheet, wherein
water being supplied from the base sheet to the heat-generative layer,
the method comprising steps of:
adding an aqueous electrolyte solution containing the electrolyte to a side of the base sheet, and
applying a coating material containing the oxidizable metal particles and not containing the electrolyte to that side of the base sheet having the aqueous electrolyte solution added thereto.

12. A method for making a heat generating device comprising a step of making a heat generating element by the method according to claim 11 and a step of entirely enclosing the resulting heat generating element in an enclosing material,
wherein the layer of the heat generative composition is made in a non-flowable state prior to enclosing the heat generating element in the enclosing material.

13. A method for making a heat generating element comprising:
a base sheet, and
a layer of a heat generative composition containing oxidizable metal particles, an electrolyte, and water on the base sheet,
the method comprising steps of:
(a) adding the electrolyte in a solid state to a side of the base sheet, and
(b) applying a coating material containing the oxidizable metal particles and water and not containing the electrolyte to the side of the base sheet,
the steps being carried out in a reverse order or simultaneously.

14. The method for making a heat generating element according to claim 13, wherein the water content is 18% to 48% by mass based on the total mass of the coating material.

15. The method for making a heat generating element according to claim 13, wherein the base sheet contains a superabsorbent polymer, and the electrolyte is added to the coated surface being in a wetted state.

* * * * *